United States Patent
Dunn et al.

(10) Patent No.: US 9,351,670 B2
(45) Date of Patent: May 31, 2016

(54) GLYCEMIC RISK DETERMINATION BASED ON VARIABILITY OF GLUCOSE LEVELS

(71) Applicant: ABBOTT DIABETES CARE INC., Alameda, CA (US)

(72) Inventors: Timothy Dunn, San Francisco, CA (US); Kenneth J. Doniger, Menlo Park, CA (US); Glenn Berman, Alameda, CA (US); Gary A. Hayter, Oakland, CA (US); Erwin S. Budiman, Fremont, CA (US); Daniel Bernstein, El Granada, CA (US); Nathan Crouther, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 483 days.

(21) Appl. No.: 13/732,184

(22) Filed: Dec. 31, 2012

(65) Prior Publication Data

US 2014/0187887 A1 Jul. 3, 2014

(51) Int. Cl.
 *A61B 5/145* (2006.01)
 *A61B 5/00* (2006.01)
 *G06F 19/00* (2011.01)

(52) U.S. Cl.
 CPC ........... *A61B 5/14532* (2013.01); *A61B 5/7275* (2013.01); *A61B 5/743* (2013.01); *G06F 19/345* (2013.01); *G06F 19/3456* (2013.01); *G06F 19/3487* (2013.01); *G06F 19/3431* (2013.01)

(58) Field of Classification Search
 CPC ... A61B 5/743; A61B 5/7275; A61B 5/14532
 See application file for complete search history.

(56) References Cited

U.S. PATENT DOCUMENTS

| 4,695,954 A | 9/1987 | Rose et al. |
| 4,731,726 A | 3/1988 | Allen, III |
| 4,779,199 A | 10/1988 | Yoneda et al. |
| 4,817,044 A | 3/1989 | Ogren |
| 5,019,974 A | 5/1991 | Beckers |
| 5,216,597 A | 6/1993 | Beckers et al. |
| 5,251,126 A | 10/1993 | Kahn et al. |
| 5,307,263 A | 4/1994 | Brown |

(Continued)

FOREIGN PATENT DOCUMENTS

| EP | 1418523 A | 12/2004 |
| GB | 2443434 A | 5/2008 |

(Continued)

OTHER PUBLICATIONS

Kovatchev, Boris P., Ph.D., et al., "Quantifying Temporal Glucose Variability in Diabetes via Continuous Glucose Monitoring: Mathematical Methods and Clinical Application," Diabetes Technology & Therapeutics, vol. 7, No. 6, 2005, pp. 849-862.

(Continued)

*Primary Examiner* — Navin Natnithithadha
*Assistant Examiner* — Meredith Weare
(74) *Attorney, Agent, or Firm* — One LLP

(57) ABSTRACT

A system and method for determining glycemic risks based on an analysis of glucose data includes visualization of hypoglycemia, variability, and hyperglycemia with a control grid, increasing the accuracy of glucose estimates using a combination of CGM and HbA1c, calculating glycemic risk by applying a probability distribution, and tailoring SMBG test schedules based on CGM use/wear.

24 Claims, 15 Drawing Sheets

(56) References Cited

U.S. PATENT DOCUMENTS

| | | | |
|---|---|---|---|
| 5,319,363 A | 6/1994 | Welch et al. |
| 5,341,291 A | 8/1994 | Roizen et al. |
| 5,376,070 A | 12/1994 | Purvis et al. |
| 5,500,854 A | 3/1996 | Uotila et al. |
| 5,558,638 A | 9/1996 | Evers et al. |
| 5,590,648 A | 1/1997 | Mitchell et al. |
| 5,626,144 A | 5/1997 | Tacklind et al. |
| 5,704,366 A | 1/1998 | Tacklind et al. |
| 5,713,856 A | 2/1998 | Eggers et al. |
| 5,772,586 A | 6/1998 | Heinonen et al. |
| 5,822,715 A | 10/1998 | Worthington et al. |
| 5,878,384 A | 3/1999 | Johnson et al. |
| 5,925,021 A | 7/1999 | Castellano et al. |
| 5,946,659 A | 8/1999 | Lancelot et al. |
| 5,960,403 A | 9/1999 | Brown |
| 5,974,389 A | 10/1999 | Clark et al. |
| 5,997,476 A | 12/1999 | Brown |
| 6,022,315 A | 2/2000 | Iliff |
| 6,024,699 A | 2/2000 | Surwit et al. |
| 6,049,764 A | 4/2000 | Stahl |
| 6,081,786 A | 6/2000 | Barry et al. |
| 6,134,504 A | 10/2000 | Douglas et al. |
| 6,144,922 A | 11/2000 | Douglas et al. |
| 6,188,988 B1 | 2/2001 | Barry et al. |
| 6,206,829 B1 | 3/2001 | Iliff |
| 6,225,901 B1 | 5/2001 | Kail, IV |
| 6,234,964 B1 | 5/2001 | Iliff |
| 6,270,455 B1 | 8/2001 | Brown |
| 6,277,071 B1 | 8/2001 | Hennessy et al. |
| 6,336,900 B1 | 1/2002 | Alleckson et al. |
| 6,338,713 B1 | 1/2002 | Chamoun et al. |
| 6,352,505 B1 | 3/2002 | Bortz |
| 6,368,273 B1 | 4/2002 | Brown |
| 6,379,301 B1 | 4/2002 | Worthington et al. |
| 6,390,986 B1 | 5/2002 | Curcie et al. |
| 6,406,426 B1 | 6/2002 | Reuss et al. |
| 6,418,346 B1 | 7/2002 | Nelson et al. |
| 6,422,061 B1 | 7/2002 | Sunshine et al. |
| 6,450,956 B1 | 9/2002 | Rappaport et al. |
| 6,524,240 B1 | 2/2003 | Thede |
| 6,540,672 B1 | 4/2003 | Simonsen et al. |
| 6,544,174 B2 | 4/2003 | West et al. |
| 6,544,212 B2 | 4/2003 | Galley et al. |
| 6,551,243 B2 | 4/2003 | Bocionek et al. |
| 6,558,351 B1 | 5/2003 | Steil et al. |
| 6,575,900 B1 | 6/2003 | Zweig et al. |
| 6,579,231 B1 | 6/2003 | Phipps |
| 6,604,050 B2 | 8/2003 | Trippel et al. |
| 6,611,846 B1 | 8/2003 | Stoodley |
| 6,635,016 B2 | 10/2003 | Finkelshteins |
| 6,635,167 B1 | 10/2003 | Batman et al. |
| 6,645,142 B2 | 11/2003 | Braig et al. |
| 6,656,114 B1 | 12/2003 | Poulsen et al. |
| 6,692,436 B1 | 2/2004 | Bluth et al. |
| 6,781,522 B2 | 8/2004 | Sleva et al. |
| 6,799,149 B2 | 9/2004 | Hartlaub |
| 6,804,558 B2 | 10/2004 | Haller et al. |
| 6,872,200 B2 | 3/2005 | Mann et al. |
| 6,915,170 B2 | 7/2005 | Engleson et al. |
| 7,241,265 B2 | 7/2007 | Cummings et al. |
| 7,920,907 B2 | 4/2011 | McGarraugh et al. |
| 8,409,093 B2 | 4/2013 | Bugler |
| 8,758,245 B2 | 6/2014 | Ray et al. |
| 2003/0216628 A1 | 11/2003 | Bortz et al. |
| 2005/0119540 A1 | 6/2005 | Potts et al. |
| 2005/0159656 A1 | 7/2005 | Hockersmith et al. |
| 2005/0187789 A1 | 8/2005 | Hatlestad et al. |
| 2005/0214892 A1 | 9/2005 | Kovatchev et al. |
| 2005/0267780 A1 | 12/2005 | Ray et al. |
| 2006/0010098 A1 | 1/2006 | Goodnow et al. |
| 2006/0106644 A1 | 5/2006 | Koo et al. |
| 2006/0173260 A1 | 8/2006 | Gaoni et al. |
| 2006/0189863 A1 | 8/2006 | Peyser et al. |
| 2006/0264895 A1 | 11/2006 | Flanders |
| 2007/0033074 A1 | 2/2007 | Nitzan et al. |
| 2008/0071580 A1 | 3/2008 | Marcus et al. |
| 2008/0154513 A1 | 6/2008 | Kovatchev et al. |
| 2008/0234943 A1 | 9/2008 | Rat et al. |
| 2008/0234992 A1 | 9/2008 | Ray et al. |
| 2008/0235053 A1 | 9/2008 | Ray et al. |
| 2008/0255438 A1 | 10/2008 | Saidara et al. |
| 2009/0105573 A1 | 4/2009 | Malecha |
| 2009/0171589 A1 | 7/2009 | Kovatchev |
| 2009/0240127 A1* | 9/2009 | Ray ............................. 600/365 |
| 2010/0332445 A1 | 12/2010 | Ray et al. |
| 2011/0264378 A1 | 10/2011 | Breton et al. |
| 2013/0035575 A1* | 2/2013 | Mayou ............... A61B 5/14532 600/365 |
| 2014/0030748 A1* | 1/2014 | Schaible ............ G06F 19/3431 435/14 |
| 2014/0088392 A1* | 3/2014 | Bernstein et al. ............. 600/365 |
| 2014/0088393 A1* | 3/2014 | Bernstein et al. ............. 600/365 |

FOREIGN PATENT DOCUMENTS

| | | |
|---|---|---|
| JP | 4348747 A | 12/1992 |
| JP | 2001245900 A | 9/2001 |
| JP | 2002132952 | 5/2002 |
| JP | 2003500744 A | 1/2003 |
| JP | 2004024699 A | 1/2004 |
| JP | 2004154547 | 6/2004 |
| WO | 0004512 A2 | 1/2000 |
| WO | 0100086 A1 | 4/2001 |
| WO | 0205702 A2 | 1/2002 |
| WO | 0215777 A1 | 2/2002 |
| WO | 2005081170 A2 | 1/2005 |
| WO | 2005065538 A2 | 7/2005 |
| WO | 2005093629 A2 | 10/2005 |
| WO | 2007005170 A2 | 1/2007 |
| WO | 2008071218 A1 | 6/2008 |
| WO | WO 2012/108939 A1 * | 8/2012 ............... A61B 5/00 |
| WO | WO PCT/US2013/078535 | 9/2014 |
| WO | WO PCT/US2013/078535 | 6/2015 |

OTHER PUBLICATIONS

Brownlee, M., et al., "Glycemic Variability: A Hemoglobin A1c—Independent Risk Factor for Diabetic Complications", JAMA, 2006, vol. 295, No. 14, pp. 1707-1708.

Kilpatrick, E. S., "The Effect of Glucose Variability on the Risk of Microvascular Complications in Type 1 Diabetes", Diabetes Care, 2006, vol. 29, No. 7, pp. 1486-1490.

Mazze, R. S., "Ambulatory Glucose Profile: Representation of Verified Self-Monitored Blood Glucose Data", Diabetes Care, 1987, vol. 10, No. 1, pp. 111-117.

Mazze, R. S., "Characterizing Glucose Exposure for Individuals with Normal Glucose Tolerance Using Continuous Glucose Monitoring and Ambulatory Glucose Profile Analysis", Diabetes Technology & Therapeutics, 2008, vol. 10, No. 3, pp. 149-159.

Wilson, D. M., "The Accuracy of the FreeStyle Navigator Continuous Glucose Monitoring System in Children With Type 1 Diabetes ", Diabetes Care, 2007, vol. 30, No. 1, pp. 59-64.

Fritzsche, G., et al., "The Use of a Computer Program to Calculate the Mean Amplitude of Glycemic Excursions", Diabetes Technology & Therapeutics, 2011, vol. 13, No. 3, pp. 319-325.

Rodbard, D., "Optimizing Display, Analysis, Interpretation and Utility of Self-Monitoring of Blood Glucose (SMBG) Data for Management of Patients with Diabetes", Journal of Diabetes Science and Technology, 2007, vol. 1, No. 1, pp. 62-71.

* cited by examiner

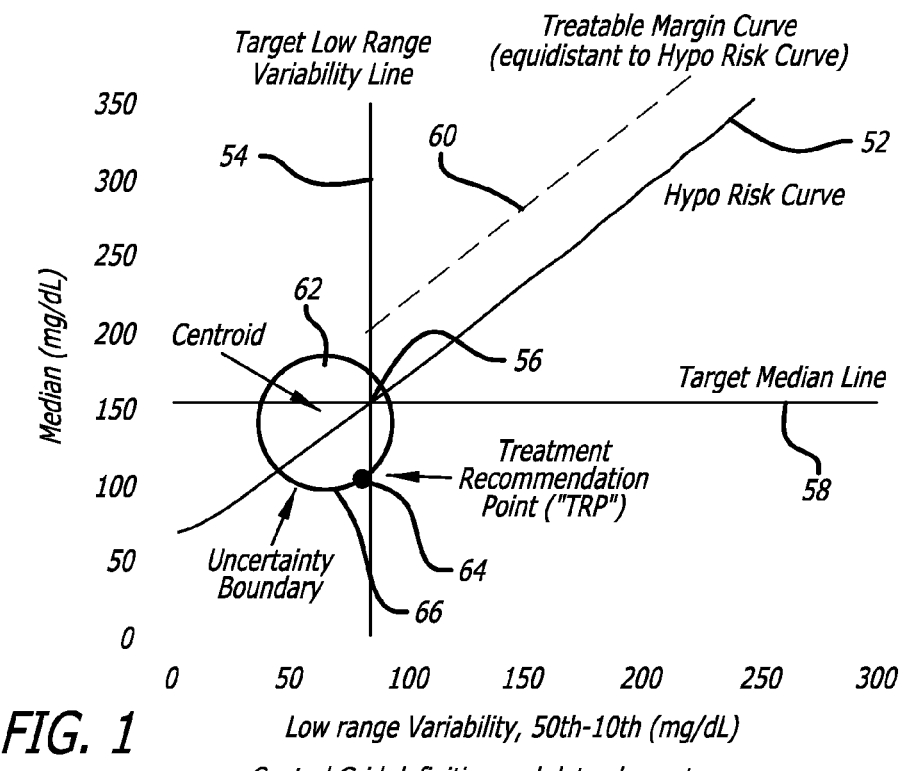
FIG. 1 Control Grid definition and data elements
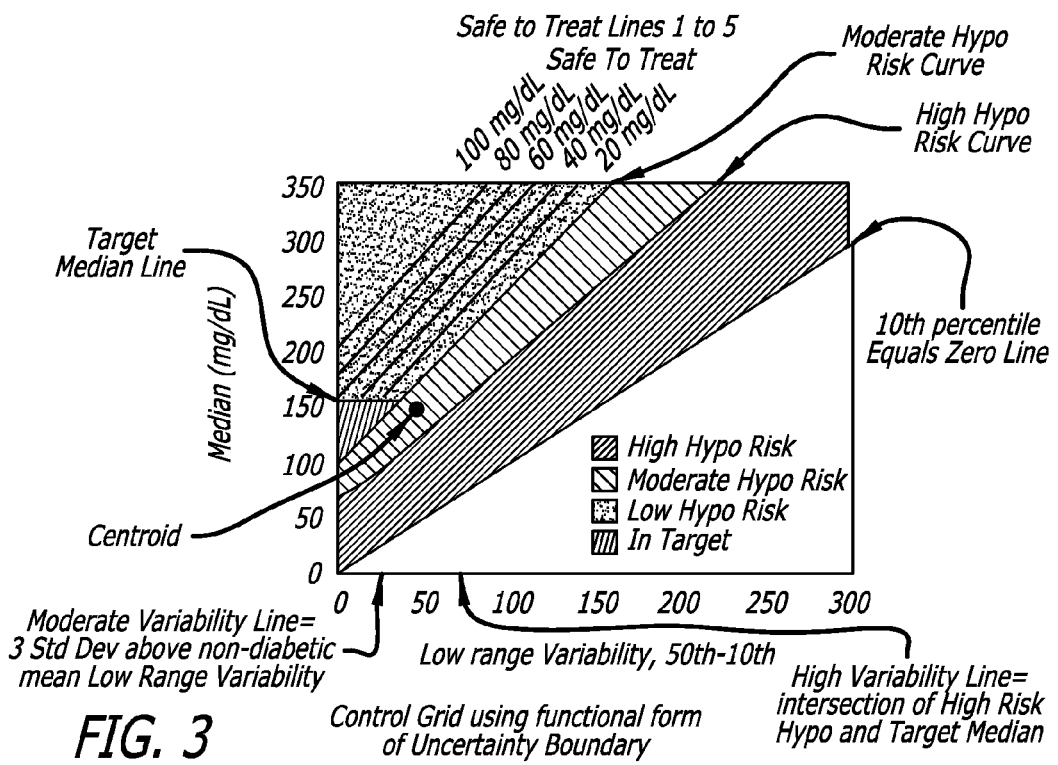
FIG. 3 Control Grid using functional form of Uncertainty Boundary Graphical definitions of Risk Reduction Distances Examples for HypoRRD Examples for HyperRRD

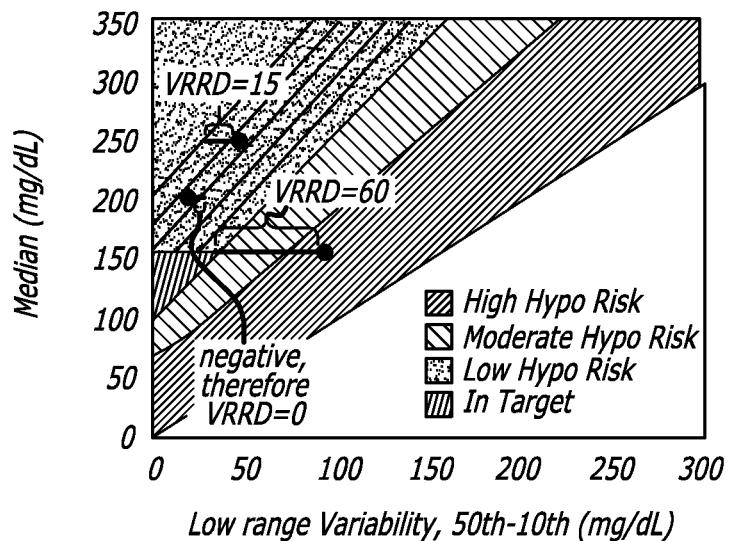
FIG. 6  Examples for VRRD
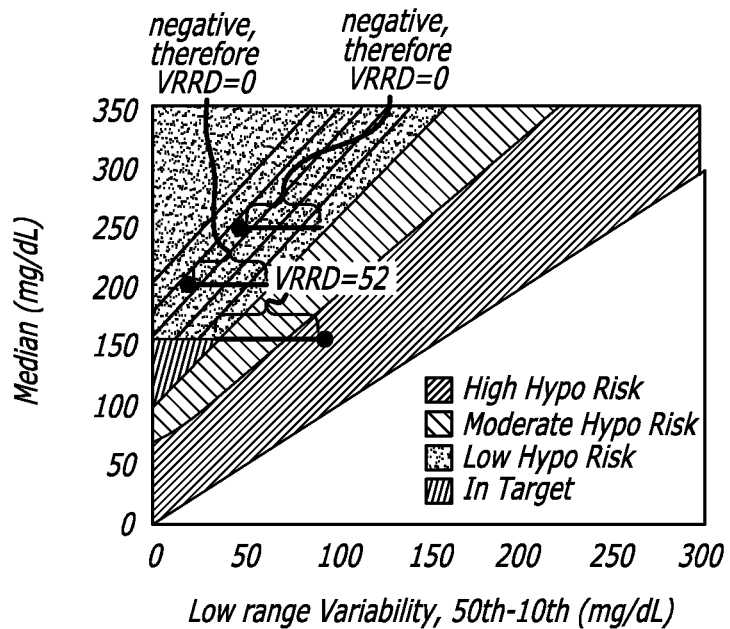
FIG. 7  Examples for VRRD, alternate definition

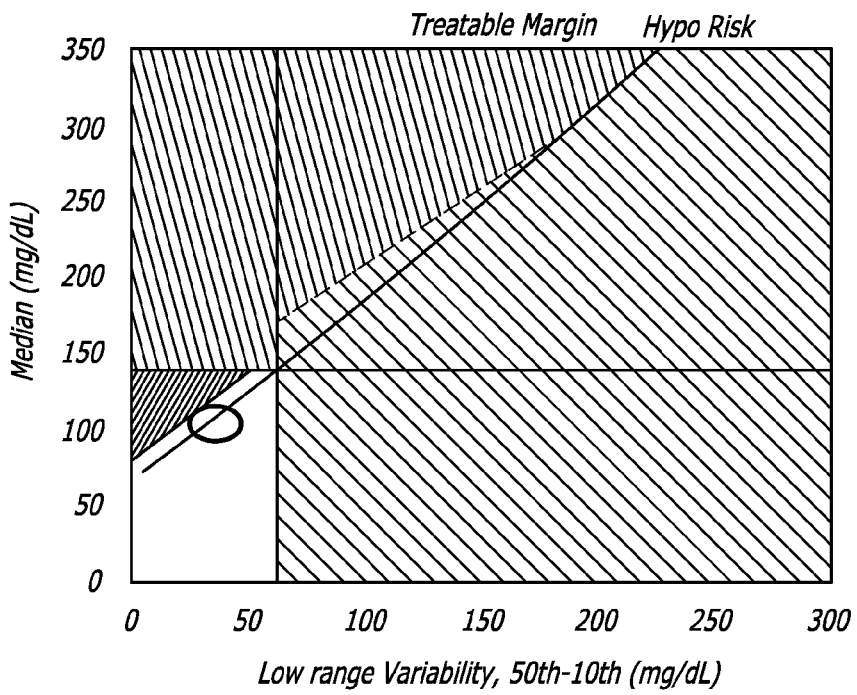
FIG. 10  Alternate design of zone definition
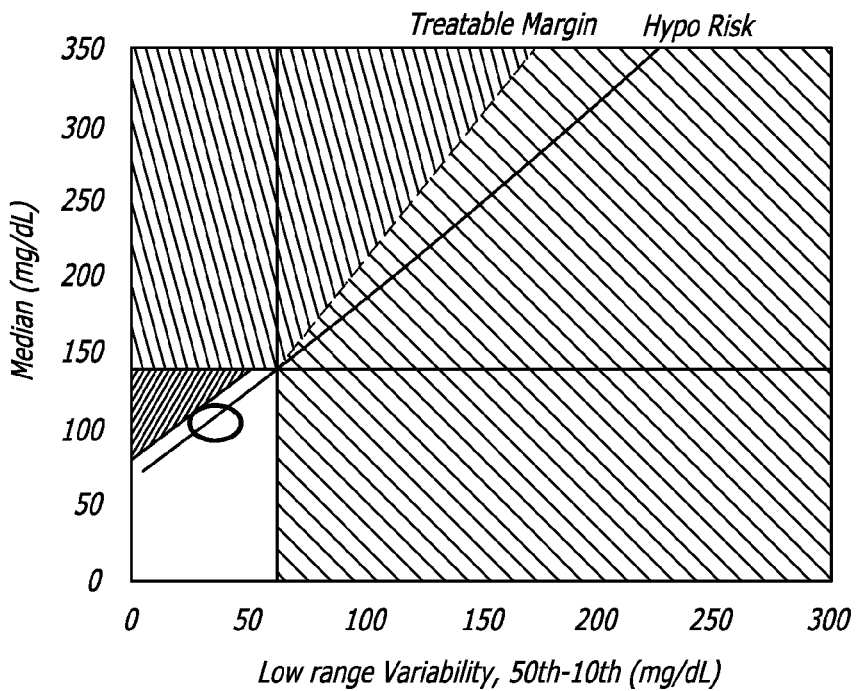
FIG. 11  Alternate design of zone definition

GLYCEMIC RISK DETERMINATION BASED ON VARIABILITY OF GLUCOSE LEVELS

BACKGROUND

The invention relates generally to medical data processing and display, and more particularly, to a system and method for collecting, analyzing, and displaying analyses of medical analyte data for managing diabetes mellitus.

Diabetes mellitus, or simply, "diabetes," is an incurable chronic disease. Type 1 diabetics must manage their diabetes by taking a glucose-lowering medication, such as insulin, to compensate for the rise in blood glucose that follows food consumption. Type 1 diabetes management works to prevent hyperglycemia, or high blood glucose, while especially averting the consequences of hypoglycemia, or low blood glucose, from over-aggressive or incorrect insulin dosing. Poor diabetes management can manifest in acute symptoms, such as loss of consciousness, or through chronic conditions, including cardiovascular disease, retinopathy, neuropathy, and nephropathy. Effective diabetes management requires effort.

Many different ways exist to assist in monitoring and managing one's glucose levels. Health care maintenance systems based on the use of a handheld device are often used. These devices are configured to record patient data, such as blood glucose data. Additionally, it is known that such data can be uploaded to a remote server for storage of large quantities of medical data and later access to it by third parties, such as the patient's health care providers ("HCP"). Examples are Google Health and Microsoft HealthVault™. At the remote server location or elsewhere, blood glucose test results can be matched with quantitative information on medication, meals, or other factors, such as exercise.

Medical sensors can generate large quantities of useful information about a physiological parameter or parameters of a patient. That information, when processed, organized, and analyzed in particular ways, can be highly beneficial to an HCP in examining the patient and recommending treatment. The appropriate calculations, organization, and analyses of that data can assist in forming rapid, useful, and more accurate evaluations of the information, the patient's history, and the patient's present state and health condition.

For example, analyte monitoring and medication delivery devices are commonly used in the treatment of a patient. One or more samples of analytes from the patient's body tissues are sensed and data is accumulated. A monitor, containing a sensor and a processor, may be used to acquire, accumulate, and process that data. Ultimately a report must be produced from that data and an analysis made by an HCP. In response to the analysis, one or more medications may be administered to the patient or other course of treatment prescribed, such as exercise and control over the timing, amount, and contents of meals. Administration of the medication may be manual by the patient such as self-injection with a syringe, by another person such as a nurse, or by a powered medication administration device, such as an infusion pump, for automatic or continuous delivery. For example, glucose monitors and insulin pumps are commonly used in the treatment and management of type 1 diabetes mellitus.

In the case of diabetes, a blood glucose monitor ("BGM") or continuous glucose monitor ("CGM") may be used in obtaining data about the glucose level of a patient. Such sensors detect glucose levels through actual analysis of a drop of blood, or through sensing the composition of interstitial tissue. The patient may have a handheld digital device, such as a personal digital assistant ("PDA") that is used to receive and store his or her glucose data. This can occur in a number of ways. In the case where the patient draws a drop of blood onto a test strip that is read by a BGM, the data from the BGM may be communicated to the PDA for storage, processing (such as by adding a date and time stamp), and transfer elsewhere.

In one case, the BGM is integrated with the PDA (dedicated device) and in another case, both the BGM and the PDA may be integrated into a mobile telephone with the appropriate hardware and software as a single unit. In another case, the glucose data is communicated to the PDA wirelessly or through a wired connection. In both cases of the BGM and CGM, various schemes may be used to get measured patient glucose data onto the PDA. The PDA is programmed to process that data and can provide a useful number representation of a glucose level on the screen of the PDA, and can also be instructed to upload the data to a server that may be remote and which may be accessed through the Internet (cloud computing) or by other means. Conveniently, a computerized report can be used to display such measurements and calculations of the measured glucose together and can be analyzed for use in developing health management recommendations. For example, glucose monitors are programmed to provide recommendations for better blood glucose management in the patient. Such analyses often include trends, extrapolations, predictions, alerts, and others.

Accordingly, the detection of the level of analytes, such as glucose, lactate, oxygen, and the like, in certain individuals is vitally important to their health. Moreover, analyzing these analytes and recording analytics relating thereto, as well as other patient behavior, such as activities and meals, and providing this information to HCPs for analysis can provide valuable, life-saving feedback to patients who have difficult medical conditions. For example, monitoring glucose levels is particularly important to individuals with diabetes as well as monitoring diet and exercise, to determine when insulin is needed to reduce glucose levels in their bodies or when additional glucose is needed to raise the level of glucose in their bodies. The provision of related analytics of their glucose levels to an HCP may result in a therapy recommendation that may be useful in helping the patient better manage his or her diabetes. Existing data management and analysis tools are available and are further being developed to assist patients along these lines.

Previous glycemic control risks have been assessed visually by trained experts who have developed skills in balancing the competing demands of consistently lowering glucose levels while avoiding excessive hypoglycemia. Typically these experts review plots or tables of glucose values. These skills are hard to acquire and transfer to others.

Self-monitoring blood glucose ("SMBG") testing schedules are assigned to patients by HCPs in order to gather data so that the HCPs can make recommendations to patients regarding therapy and lifestyle changes. Key metrics that can be ascertained by this SMBG testing are median glucose, low range variability, and hypoglycemia risk. Typically a key therapy goal is to reduce a patient's median glucose while avoiding the risk of the patient spending significant time in hypoglycemia or experiencing a severe hypoglycemia incidence. The higher a patient's low range variability, the higher the median glucose the patient will need to maintain in order to avoid these incidences of hypoglycemia.

Some of the problems with SMBG testing schedules are patient compliance and limited data. Patients may not comply with an SMBG testing schedule because blood glucose ("BG") testing can be painful and inconvenient. In order to maximize compliance, SMBG test schedules generally occur over a short time period with just a handful of SMBG tests.

This leads to the second problem, limited data. SMBG testing schedules will produce relatively small data sets which can introduce a high uncertainty to the calculated median glucose, calculated low range variability, and calculated hypoglycemia risk. The higher the uncertainty, the less aggressive the treatment recommendations can be in order to be sure that the hypoglycemia risks are avoided.

Additionally, another problem caused by collecting a small amount of data is that SMBG measurements can either be focused on a small number of short time periods or long time periods, but not both. For example, an SMBG test schedule might focus on median and variability at fixed times, for example one hour after meals, requiring the patient to perform tests every day for one to two weeks one hour after each scheduled meal. With such a test schedule, the median and low range variability can be calculated relatively accurately, but only for one hour after each scheduled meal. Little information will be learned about other time periods (such as two hours after each meal). Alternatively, the SMBG test schedule may follow a progressive schedule requiring the patient to test at various times of the day. For example the schedule might ask for the patient to test at 7:00 AM, 11:00 AM, 3:00 PM, and 7:00 PM one day, and then 8:00 AM, 12:00 PM, 4:00 PM, and 8:00 PM the next day for one to two weeks. This type of SMBG test schedule can produce a relatively accurate portrayal of median and low range variability during the entire range of times tested. It is unlikely that a patient will comply with a testing schedule that requires a test during sleeping hours day after day.

Continuous glucose monitors ("CGMs") are also given to patients by HCPs to measure a patient's median glucose, low range variability, and hypoglycemia risk. By using a CGM, most of the problems associated with discrete blood glucose testing with BGMs can be addressed. With a CGM, one typically doesn't need to worry about patient compliance. There is enough data to measure low range variability to very small time periods, typically as short as one hour. Additionally, CGM systems provide data while the patient is sleeping.

The drawbacks of CGM are that it is relatively expensive, it can be uncomfortable, and patients must typically wear a device continuously, day and night, which many are very reluctant to do. It would therefore be helpful if a patient were able to wear a CGM for shorter periods of time, yet still obtain enough useful data to more accurately monitor and manage blood glucose.

Hence, those skilled in the art have recognized that there is a need for a system and a method that more accurately determine blood glucose levels in a patient. Another recognized need is for requiring the more useful and efficient collection of blood glucose data from patients so that patients will have a higher compliance level with a testing schedule. Another need is for an analysis system and method of the blood glucose data of a patient to consider variation in blood glucose levels so that glycemic risk can be determined and better treatment can result. A further need is for a clearer analysis and display of glucose data so that treatment can be prescribed with a small risk that varying blood glucose levels may cause hypoglycemic incidence. The present invention fulfills these needs and others.

SUMMARY OF THE INVENTION

Briefly and in general terms, the present invention is directed to a system and method for determining glycemic risks and include visualization of hypoglycemia, variability, and hyperglycemia with a control grid and other displays, increasing the accuracy of glucose estimates using a combination of CGM and HbA1c, calculating glycemic risk by applying a probability distribution, and tailoring SMBG test schedules based on CGM use/wear.

In one aspect there is provided a system for determining glycemic risk based on analysis of glucose data, the system comprising a non-volatile memory in which is stored a glucose data processing program configured to program a processor to analyze received glucose data and from the analysis, produce a display, an input at which glucose data is received, a display on which glucose data and analytics thereof may be visually presented, a processor connected with the nonvolatile memory, the input, and the display, the processor being configured to access the memory to load and run in the processor the program to analyze glucose data, wherein the processor is programmed to analyze the received glucose data to determine a glucose median, a low range variability of glucose, and a hypoglycemia risk, and control the display to visually present glycemic risks of hypoglycemia and glucose variability for different times of the day, and thereby allow investigation and illustration of how changes in glucose levels could affect those risks, whereby periods of the day needing a reduction in hypoglycemia and/or a reduction in glycemic variability can be seen.

In other more detailed aspects, the glucose processing program further programs the processor to control the display to visually present a control grid on which is shown a hypoglycemia risk curve and a glucose variability curve and also showing risk reduction distances for hypoglycemia and glucose variability. The glucose processing program further programs the processor to control the display to visually present on the control grid a treatment recommendation point. The glucose processing program further programs the processor to control the display to visually present on the control grid an uncertainty boundary. The glucose processing program further programs the processor to control the display to visually present on the control grid a hyperglycemia curve and a risk reduction distance for hyperglycemia.

In yet other detailed aspects, the glucose processing program further programs the processor to control the display to visually present a graphical representation of risk reduction showing hyperglycemia and glucose variability separately. The glucose processing program further programs the processor to control the display to visually present graphs representing risk reduction showing hyper and hypo combined with glucose variability.

In further aspects, the system comprises a touch screen associated with the display, wherein the glucose processing program further programs the processor to receive input from the touch screen and control the display to visually present changes in hypoglycemia risk resulting from input from the touch screen showing alteration in glucose median and/or glucose variability. The glucose processing program further programs the processor to receive HbA1c data, analyze the HbA1c data with the glucose data, determine an estimate of average glucose; and control the display to visually present the estimate of average glucose. The glucose processing program further programs the processor to subject the glucose data to an analysis of probability distribution in determining glycemic risk.

Additional aspects include the glucose processing program further programming the processor to control the display to visually present a hypoglycemic risk curve and blood glucose variability on a time period scale whereby the visual presentation on a time period scale indicates how an SMBG test schedule may be tailored to obtain further desired glucose data.

In method aspects of the invention, there is provided a method comprising the steps of storing in a non-volatile memory a glucose data processing program configured to program a processor to analyze received glucose data and from the analysis, produce a display, receiving glucose data, accessing the non-volatile memory and loading and running the glucose data processing program, analyzing the received glucose data to determine a glucose median, a low range variability of glucose, and a hypoglycemia risk, controlling a display to visually present glycemic risks of hypoglycemia and glucose variability for different times of the day, thereby allowing investigation and illustration of how changes in glucose levels could affect those risks, whereby periods of the day needing a reduction in hypoglycemia and/or a reduction in glycemic variability can be seen.

In more detailed method aspects, the glucose processing program further programs the processor for controlling the display to visually present a control grid on which is shown a hypoglycemia risk curve and a glucose variability curve and also showing risk reduction distances for hypoglycemia and glucose variability. The glucose processing program further programs the processor for controlling the display to visually present on the control grid a treatment recommendation point. The glucose processing program further programs the processor for controlling the display to visually present on the control grid an uncertainty boundary. The glucose processing program further programs the processor for controlling the display to visually present on the control grid a hyperglycemia curve and a risk reduction distance for hyperglycemia. The glucose processing program further programs the processor for controlling the display to visually present a graphical representation of risk reduction showing hyperglycemia and glucose variability separately.

In even further method aspects, the glucose processing program further programs the processor for controlling the display to visually present graphs representing risk reduction showing hyper and hypo combined with glucose variability. The glucose processing program further programs the processor for receiving input from a touch screen and controlling the display to visually present changes in hypoglycemia risk resulting from input from the touch screen showing alteration in glucose median and/or glucose variability. The glucose processing program further programs the processor for receiving HbA1c data, analyzing the HbA1c data with the glucose data, determining an estimate of average glucose, and controlling the display to visually present the estimate of average glucose.

In additional aspects, the glucose processing program further programs the processor for subjecting the glucose data to an analysis of probability distribution in determining glycemic risk. The glucose processing program further programs the processor for controlling the display to visually present a hypoglycemic risk curve and blood glucose variability on a time period scale, whereby the visual presentation on a time period scale indicates how an SMBG test schedule may be tailored to obtain further desired glucose data.

Various features and advantages of the invention will become more apparent by the following detailed description of several embodiments thereof with reference to the attached drawings.

BRIEF DESCRIPTION OF THE DRAWINGS

FIG. 1 shows a control grid definition with data elements;
FIG. 3 is the control grid using a functional form of uncertainty;
FIG. 6 shows examples of VRRD.
FIG. 7 shows an alternate definition for variability risk reduction distances;
FIG. 10 shows another alternate design of zone definition as in FIG. 9;
FIG. 11 is yet another alternate design of zone definition.

DETAILED DESCRIPTION OF THE PREFERRED EMBODIMENTS

Figure 2:
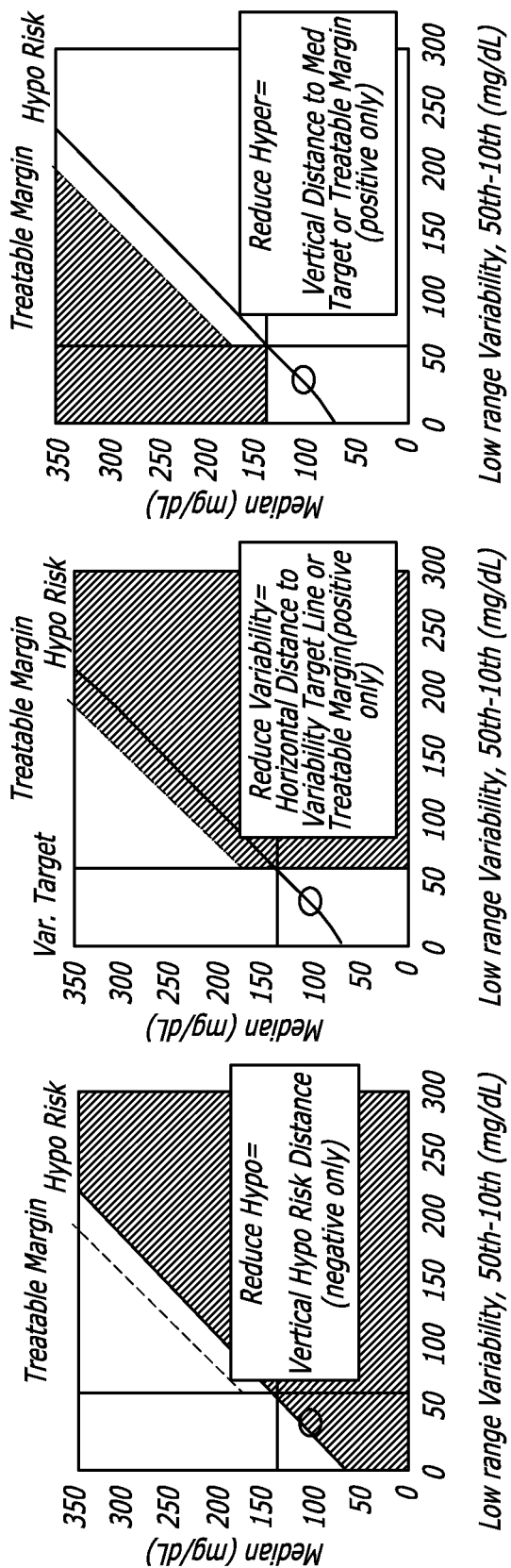
FIG. 2 is a combination of three graphs showing a reduction in hypoglycemia risk in the left diagram, reduction in variability risk in the center graph, and reduction in hyperglycemia risk in the right graph.

Reference will now be made in more detail to the drawings, wherein like reference numerals refer to like elements throughout. In one aspect the invention provides a system and a method for the calculation and visualization of glycemic risks. With more particularity, the invention provides a system and a method for determining the glycemic risks of hypoglycemia, variability, and hyperglycemia for different times of the day for a patient, and allows investigation and illustration of how changes in glucose levels could affect those risks. The invention allows rapid identification of periods of the day needing a reduction in hyperglycemia, a reduction in hypoglycemia, and/or a reduction in glycemic variability.

The present invention improves the state-of-the-art by calculating glycemic risks based on thresholds that can be customized to fit patient-specific criteria. The visualization method enables rapid illustration of problems, and supports the training of patients and non-expert care givers in the assessment of glycemic control and options for intervention. The interactive controls reinforce illustrating the effect of different intervention strategies on glycemic risks during the day.

The current invention provides a means of guiding diabetes treatment intervention by calculating the clinical risk associated with three different parameters of glucose control:
1) hypoglycemia risk;
2) glucose variability risk; and
3) hyperglycemia risk.
In all cases, the clinical goal is to reduce and ultimately remove all sources of risk. These calculated, visual representations are provided to enable quick, efficient, and intuitive identification of problem areas. Furthermore, interactive simulations of glucose management interventions can be applied to illustrate the impact of different treatment approaches.

Calculation of "Risk Reduction Amount"

The calculation of clinical risk along the three parameters of low glucose, high glucose, and glucose variability is enabled by using the concept of the "Control Grid" shown in FIG. 1, which plots the glucose median relative to the difference of the median minus tenth percentile glucose for a given set of glucose measurements (defined as "Low Range Variability" or "LRV"), for use in mapping diabetes treatment recommendations. FIG. 1 shows the control grid 50 with various data elements.

The Control Grid 50 of FIG. 1 graphically represents the calculations to be undertaken, and illustrates the selection of targets needed to define the calculations. Adjustment of the targets is allowed to individualize the risk according to different attributes of the patient under consideration. Four potential thresholds are described here:

1) target median;
2) hypoglycemia risk curve ("Hypo Risk Curve);
3) target low range variability; and
4) treatable margin curve.

Target Median—the target median curve represents the overall level of glucose control, and would typically be in the range of 125 to 155 for most patients. Lower values are associated with reduced development of health complications, such as kidney, eye, and nerve disease.

Hypoglycemia Risk Curve—the hypoglycemia risk curve 52 is defined by a theoretically constant acceptable amount of hypoglycemia. Selection of a curve higher to the left on the control grid 50 would be indicated for a patient at higher-than-normal vulnerability to low-glucose complications (such as hypoglycemia unawareness), while a curve lower to the right might be indicated for a patient at lower-than-normal vulnerability (due to continuous glucose monitor use with low glucose alarms) or a patient with other high-priority goals, such as the case with pregnancy when the tradeoff of acute low glucose symptoms is preferred to the development of fetal complications.

Target Low Range Variability—the target low range variability line 54 may be adjustable or fixed. When adjustable, it may be constrained to be the x-axis value at the point of intersection 56 of the target median line 58 and the hypo risk curve 52, or could be located at a lower value than this intersection point. In all cases, having the target low range variability line farther to the left will indicate increased risk related to glucose variability, keeping everything else equal. Currently, there is limited direct clinical evidence on the long-term benefits of reduced glucose variability, though in the context of the control grid 50, reduction of low range glucose variability is a means to reduce hypoglycemia risk.

The Treatable Margin—the concept of "treatable margin" and the treatable margin curve 60 is the amount of median glucose reduction expected when a diabetes therapy is added. It is intended to serve as a "buffer zone" to avoid treatments that may result in a mismatch in clinical risk-benefit, where a reduction in hyperglycemia risk results in an unacceptably large increase in hypoglycemia risk. Typical treatment margins would be in the range of 10 to 50 mg/dL. Adjustment would be appropriate for different types of treatments or known treatment efficacy for a particular patient. For example, clinical experience may show a diabetes drug to have a 5 mg/dL mean reduction per unit dose in Patient A, yet a 10 mg/dL mean reduction per unit dose in Patient B.

Referring again to FIG. 1, it is envisioned that any point on the control grid (x,y) 50 may be defined by either the centroid 62 or treatment recommendation point 64, or a mixture for different risk calculations. The centroid is defined as the most likely location point on the control grid 50 derived from a sample of glucose measurements. Statistical methods can be used to estimate the uncertainty bubble around the centroid, and the uncertainty boundary 66 is defined by selecting an acceptable uncertainty (for example 5% for outlining a 95% confidence region). Alternately, functional definitions of the uncertainty bubble can be found empirically. The treatment recommendation point 64 is defined as the point on the control grid that is the intersection of the uncertainty boundary and the highest-valued hypoglycemia risk curve from the surface of continuous hypo risk. From these definitions, at any point on the control grid, defined as (x,y), calculations can be made for three categories of risk, or "risk reduction distances" (shown graphically in FIG. 2).

Referring now to FIG. 2 in detail, three graphs are presented, each of which shows risk reduction distances. The graph at the left shows reduction in hypoglycemia risk. The center graph shows reduction in variability risk, and the graph at the right shows reduction in hyperglycemia risk. In particular:

Left graph—Hypoglycemia Risk Reduction Distance ("Hypo RRD")=7-Hypo Risk Curve Median Value at x (negative values only). Because of the acute risk associated with hypoglycemia, (x,y) in this case may be defined as the TRP.

Center graph—Variability Risk Reduction Distance ("VRRD")=Minimum [x−Target Low Range Variability, x−Treatable Margin Variability at y] (positive values only)

Right graph—Hyperglycemia Risk Reduction Distance ("Hyper RRD")=Minimum [y−Target Median, y−Treatable Margin Median at x] (positive values only)

Figure 4:
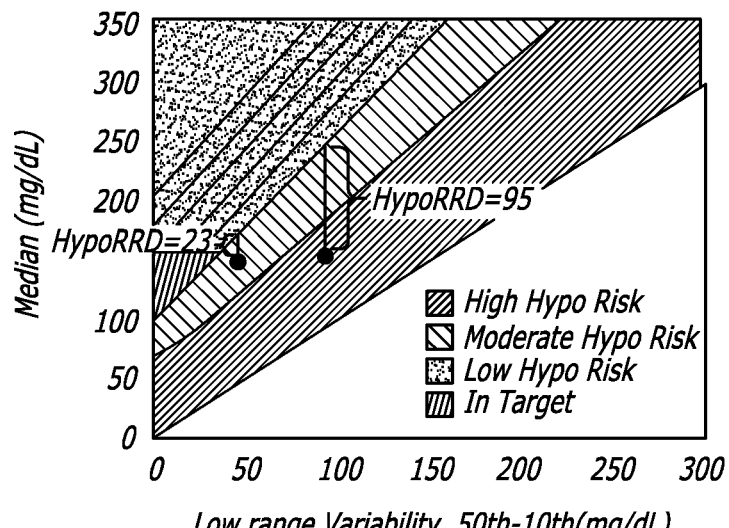
FIG. 4 shows examples of hypoglycemia risk reduction distances.

Using a functional definition of the uncertainty bubble which varies only on low range variability ("LRV") and number of glucose measurements results in a Control Grid shown in FIG. 3. Turning now to FIG. 3, there is shown a control grid using a functional form of the uncertainty boundary. Using this Control Grid, the Risk Reduction Distances are formulated with (x,y) as the Centroid by:

Hypo RRD=y-Moderate Hypo Risk Curve at x (negative values only) (see FIG. 4)

Figure 5:
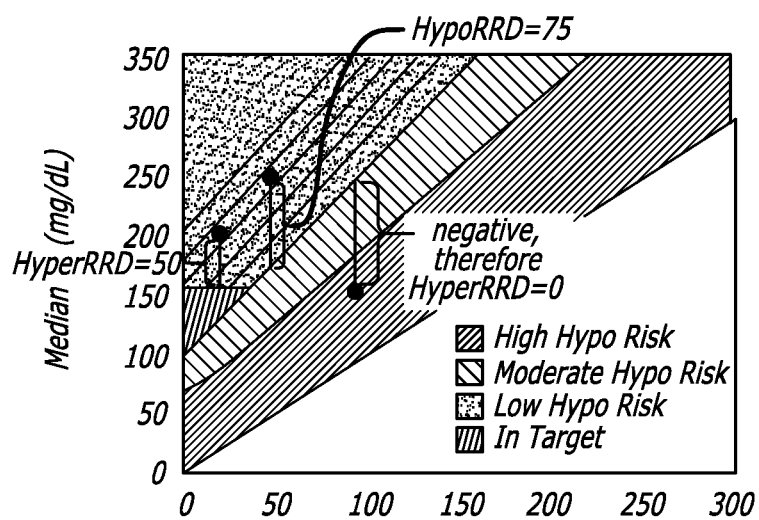
FIG. 5 shows examples of hyperglycemia risk reduction distances.

Hyper RRD=Minimum [y-Target Median, y-Moderate Hypo Risk Curve at x] (positive values only) (see FIG. 5)

VRRD=x-Moderate Variability Line (positive values only) (see FIG. 6)

Or, alternatively, to make VRRD and Hyper RRD mutually exclusive:

VRRD=Minimum [x-Moderate Variability Line, x-Treatable Margin Variability at y] (positive values only) (see FIG. 7)

Figure 8:
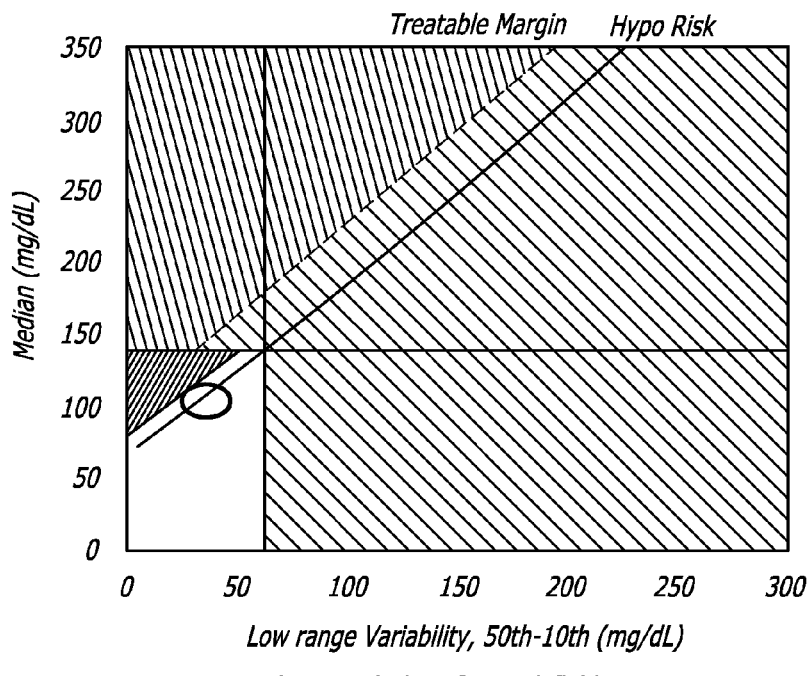
FIG. 8 provides an alternate design of zone definition.

Alternate Control Grid—given the definitions for calculating the three parameters of clinical risk, alternate underlying forms of the control grid regions may be designed in order to emphasize different clinical approaches, particularly balancing reductions in variability with reductions in hyperglycemia. One alternate design of zone definition is shown in FIG. 8 which would extend the Treatable Margin Curve parallel to the Hypo Risk Curve all the way to the Target Median Line. This design emphasizes reductions in Variability over reductions in Hyperglycemia as one approaches the Target zone at higher low range variability. This may be preferable in order to reduce the possibility of "overshooting" the Target Zone, and ending up with excessive Hypoglycemia Risk.

Figure 9:
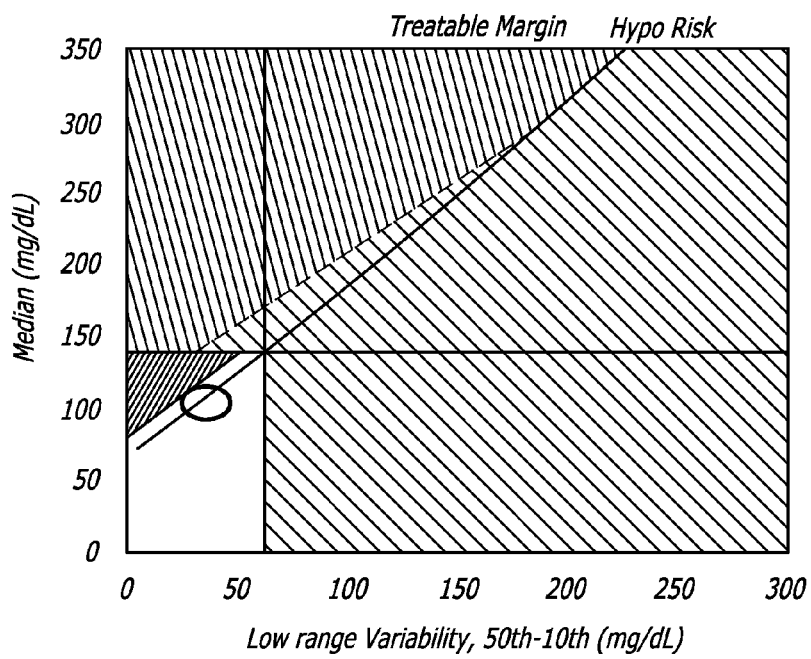
FIG. 9 shows another alternate design of zone definition.

Another alternate design of zone definition as shown in FIGS. 9 and 10 would have the Treatable Margin Curve become closer to, and eventually become equal to, the Hypo Risk Curve as low range variability increases. This design would emphasize reductions in variability at lower median and low range variabilities, but would emphasize reductions in Hyperglycemia at higher median and low range variabilities. This may be appropriate if it is deemed less acutely risky to address high glucose in the face of low glucose risk. This may be implemented either extending the Treatable Margin Curve to the Target Median (FIG. 9) or to the Target Variability line (FIG. 10).

Yet another alternate design of zone definition shown in FIG. 11 would have the Treatable Margin Curve become farther away from the Hypo Risk Curve as low range variability increases. This design would further emphasize reductions in Variability at higher median and low range variabilities. This may be appropriate if it is deemed more acutely risky to address high glucose in the face of low glucose risk.

It is envisioned that (x,y) may be defined by either the Centroid or Treatment Recommendation Point, or other points on the Uncertainty Boundary, or a mixture for different Risk Calculations. For example, a Risk calculation may be performed, and then performed a second time with a point from the Uncertainty Boundary to add additional information about the certainty of the Risk calculation. This uncertainty could be displayed numerically (below) or graphically (see "Graphical Representation" below). For example:

Hypo RRD=10 mg/dL with a 95% confidence boundary of 35 mg/dL meaning that an increase of 10 mg/dL would move the Centroid above the Hypo Risk Curve, while an increase of 35 mg/dL would move the TRP above the Hypo Risk Curve.

Graphical Representation

Once Risk calculations have been performed, they may be displayed graphically for rapid interpretation. Depending on the nature of the glucose measurements, it may be appropriate to calculate risk during different time segments. For sensor-derived glucose, it is likely to calculate hourly determinations of risk. For strip-derived glucose, it is likely to calculate determinations of risk during several, for example four or more, time periods of the day.

Figure 12:
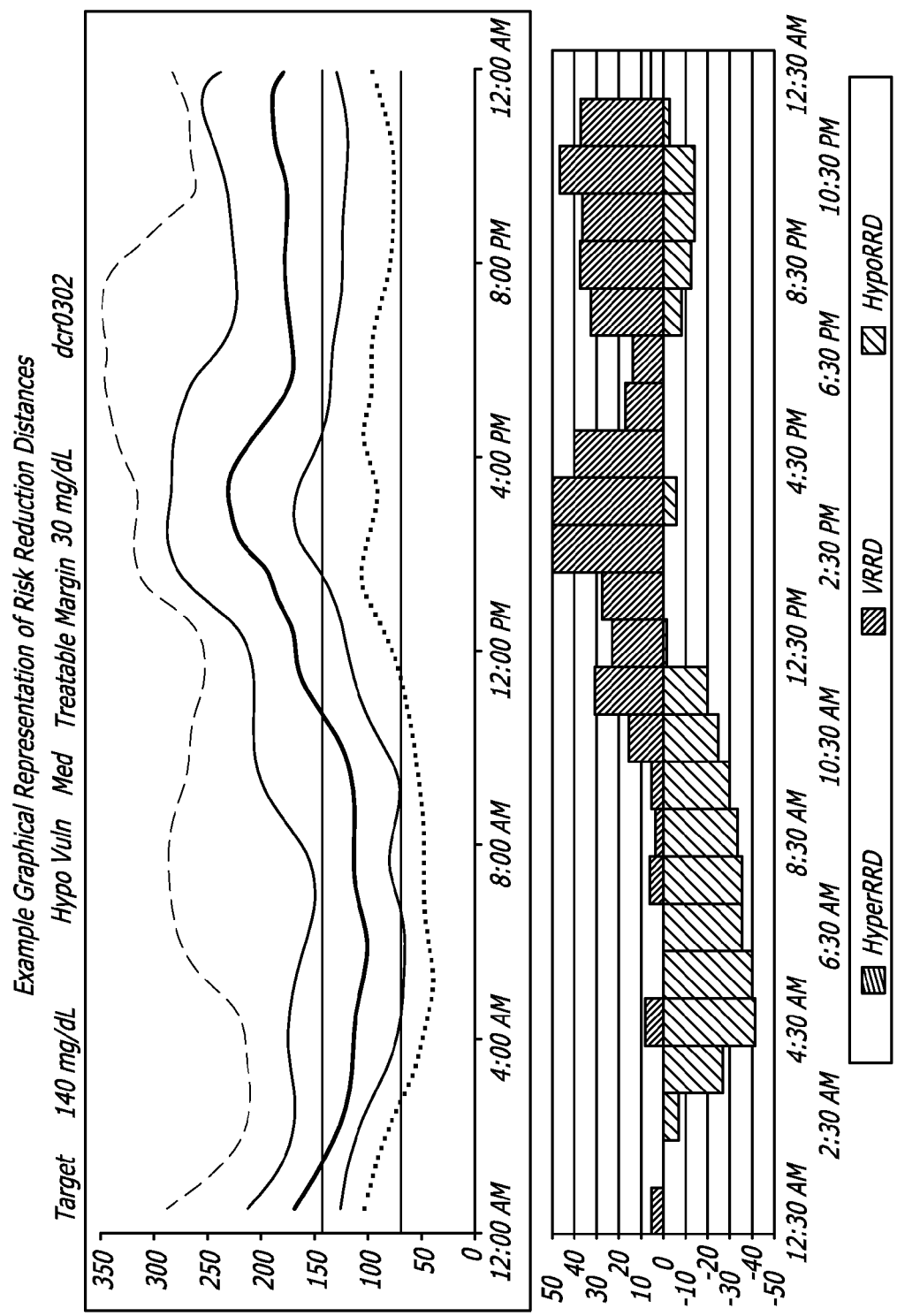
FIG. 12 is a design display of an example graphical representation of risk reduction distances.
Figure 13:
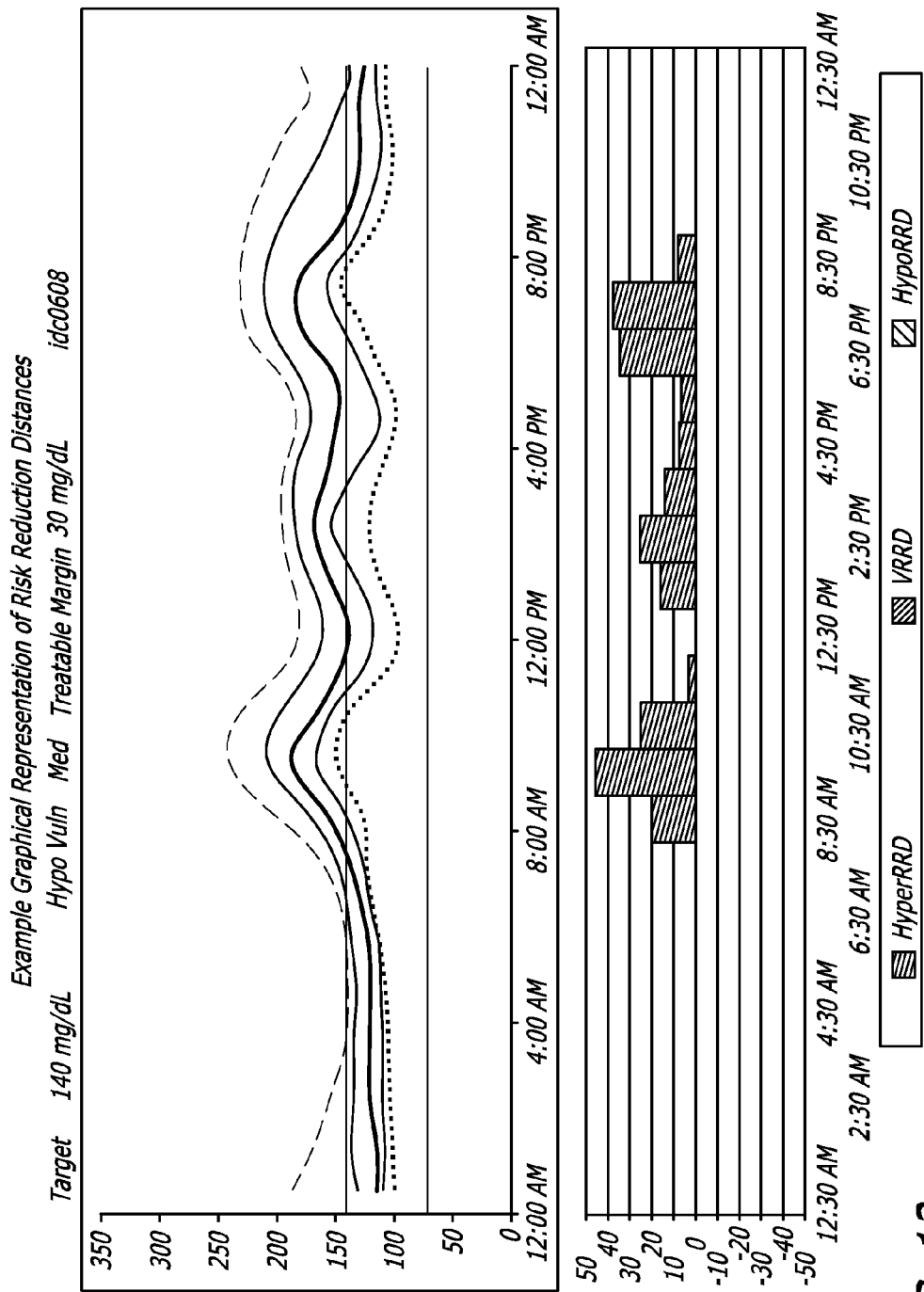
FIG. 13 is a design display of an example graphical representation of risk reduction distances.

In one embodiment of the proposed design displays shown in FIGS. 12 and 13 in which hourly data from a sensor is shown, three risk calculations are shown as vertically-aligned bars, with Hypoglycemia Risk below a horizontal line, while Variability Risk and Hyperglycemia Risk are above the line. One embodiment of the invention defines Hyper RRD and VRRD as mutually exclusive. In another embodiment, however, they could be calculated and displayed together (FIG. 13).

Figure 14:
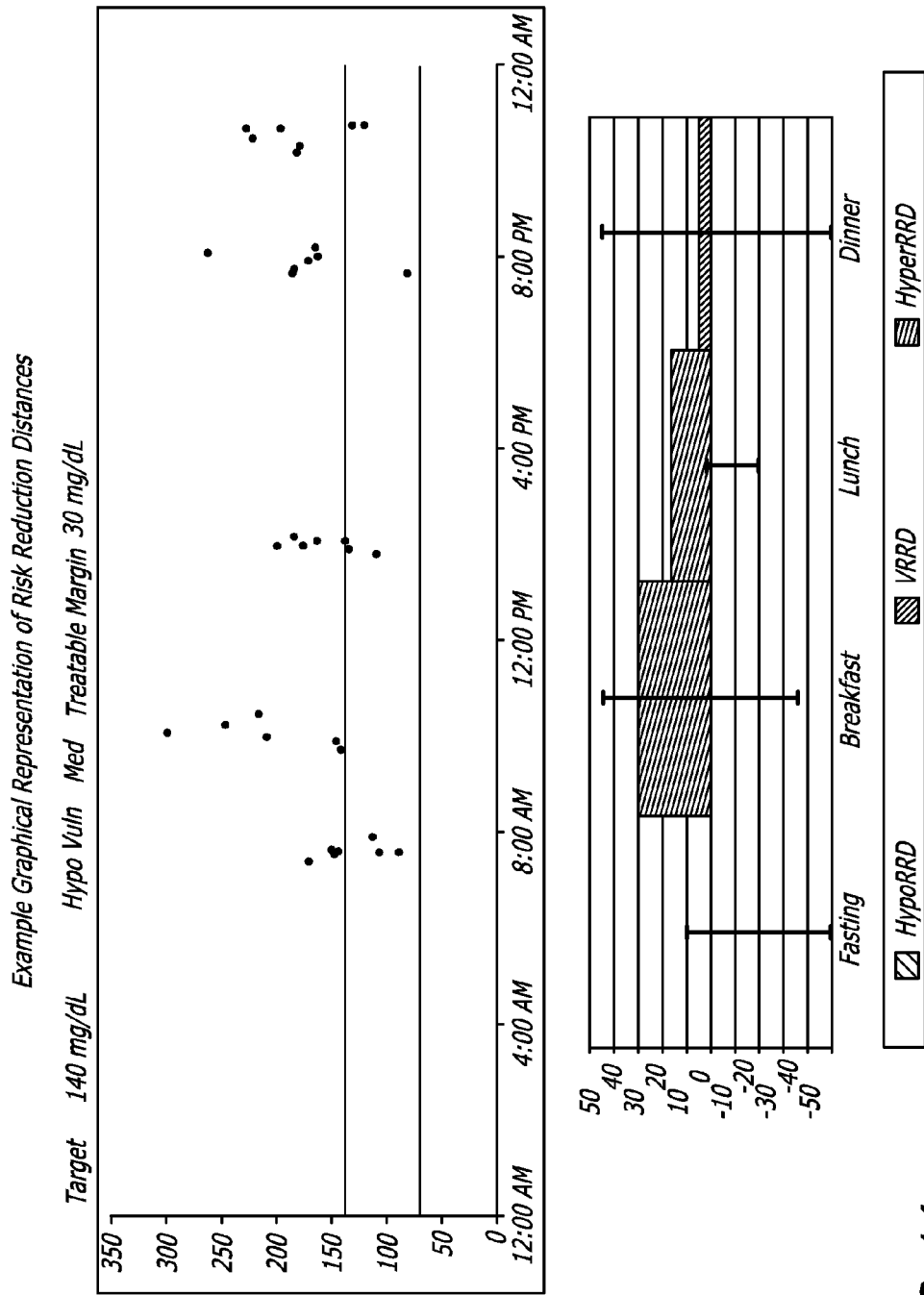
FIG. 14 provides design displays of risk reduction distances based on time periods from SMBG or a sensor.

In the graphical representation of risk reduction distances example shown in FIG. 14 based on time periods from SMBG or a sensor, the strip-derived glucose values are displayed with risk calculations in four time periods (during which the patient performed five measurements per day). In addition, the uncertainty is displayed as small "error bars" on the larger risk reduction bars.

Interactivity, "Simulation" and User Interface Controls

In order to better understand the risk associated with a set of glucose measurements, and the potential for altering the risk, additional controls have been designed. These controls allow interactive alteration of the data, allowing "what if" scenarios to be constructed. These allow further understanding of what changes may increase or decrease different sources of risk.

Control Actions

Figure 15:
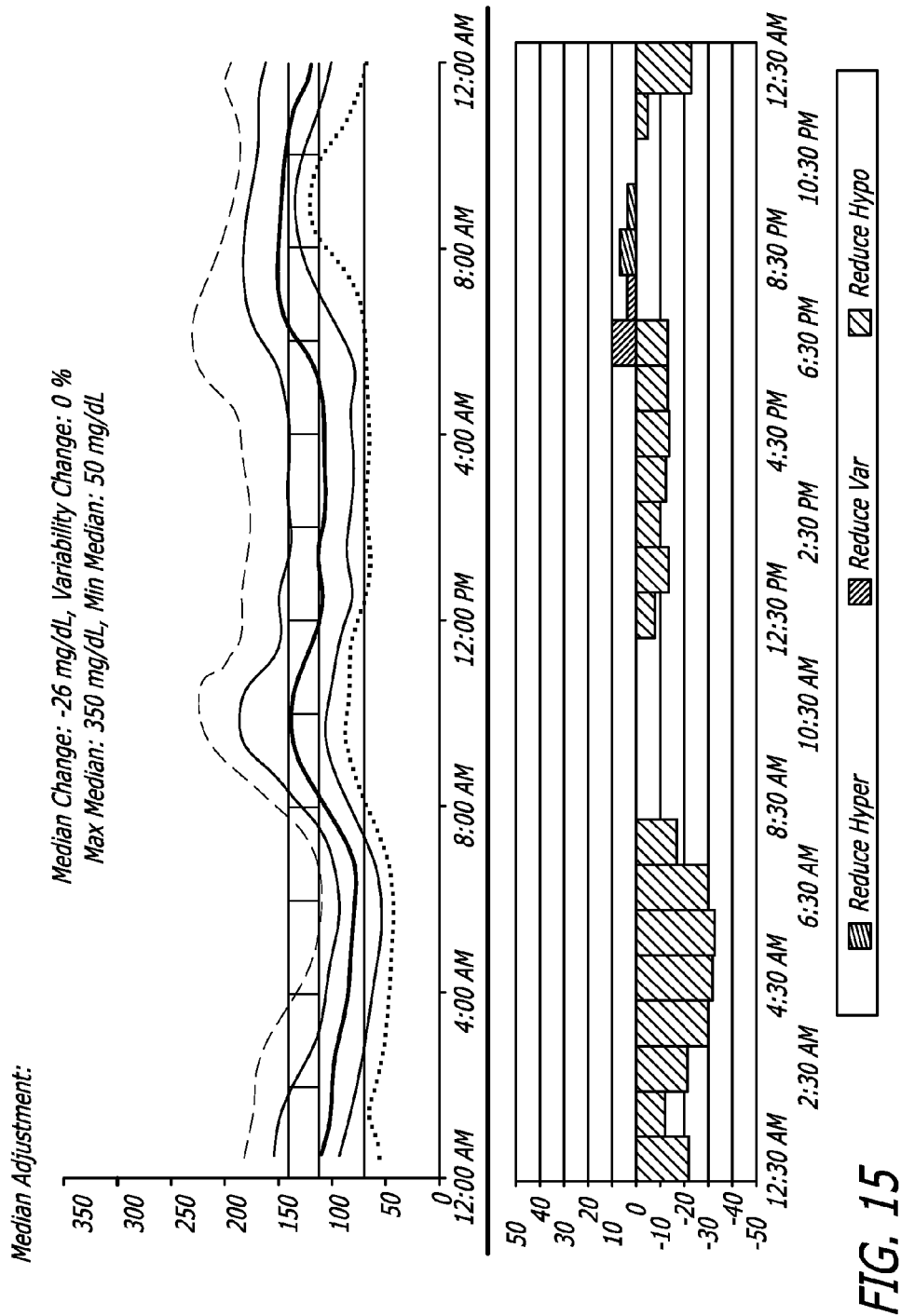
FIG. 15 presents a display of Median Adjustment having added visual features.
Figure 16:
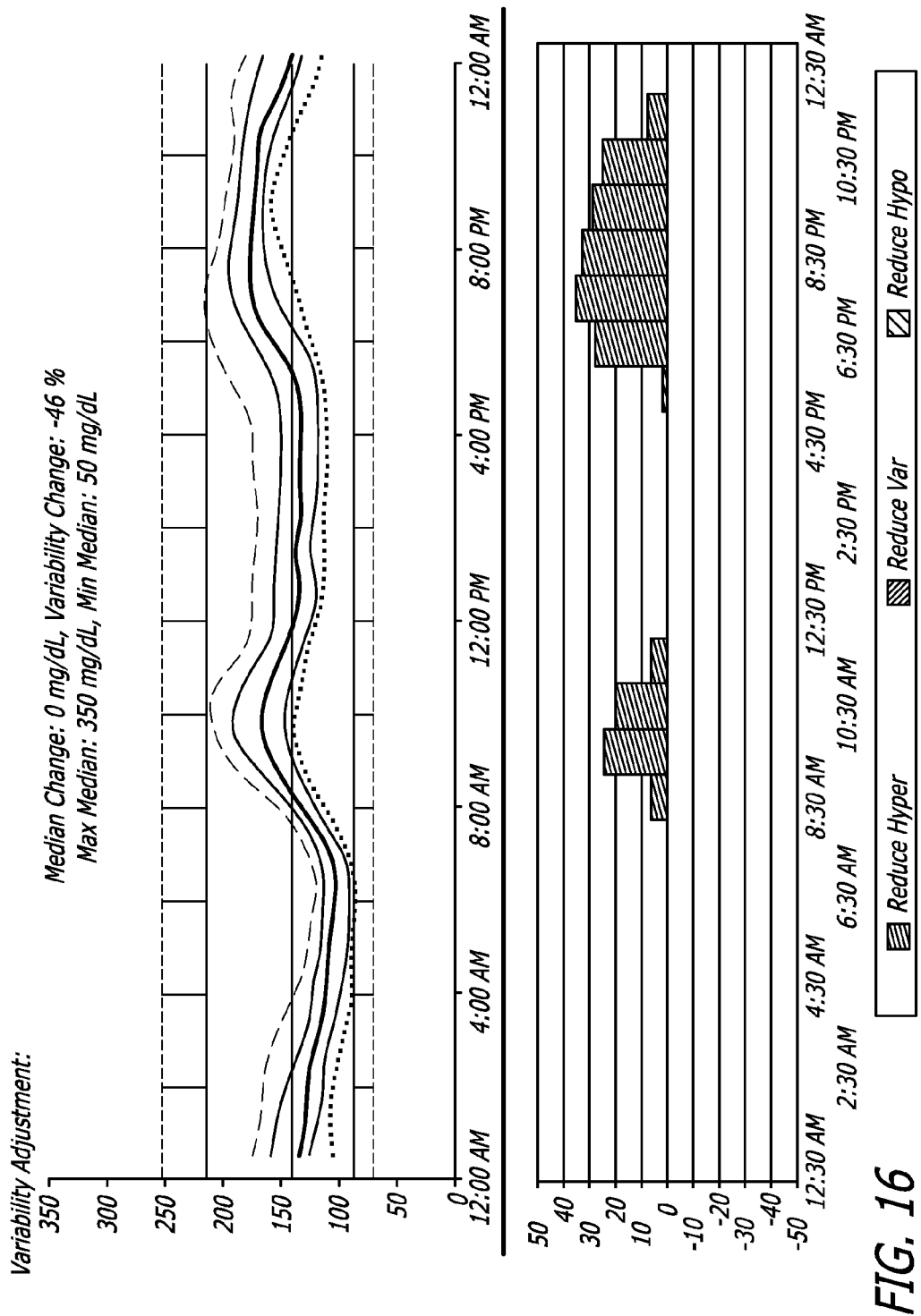
FIG. 16 presents a display of Variability Adjustment having added visual features.
Figure 17:
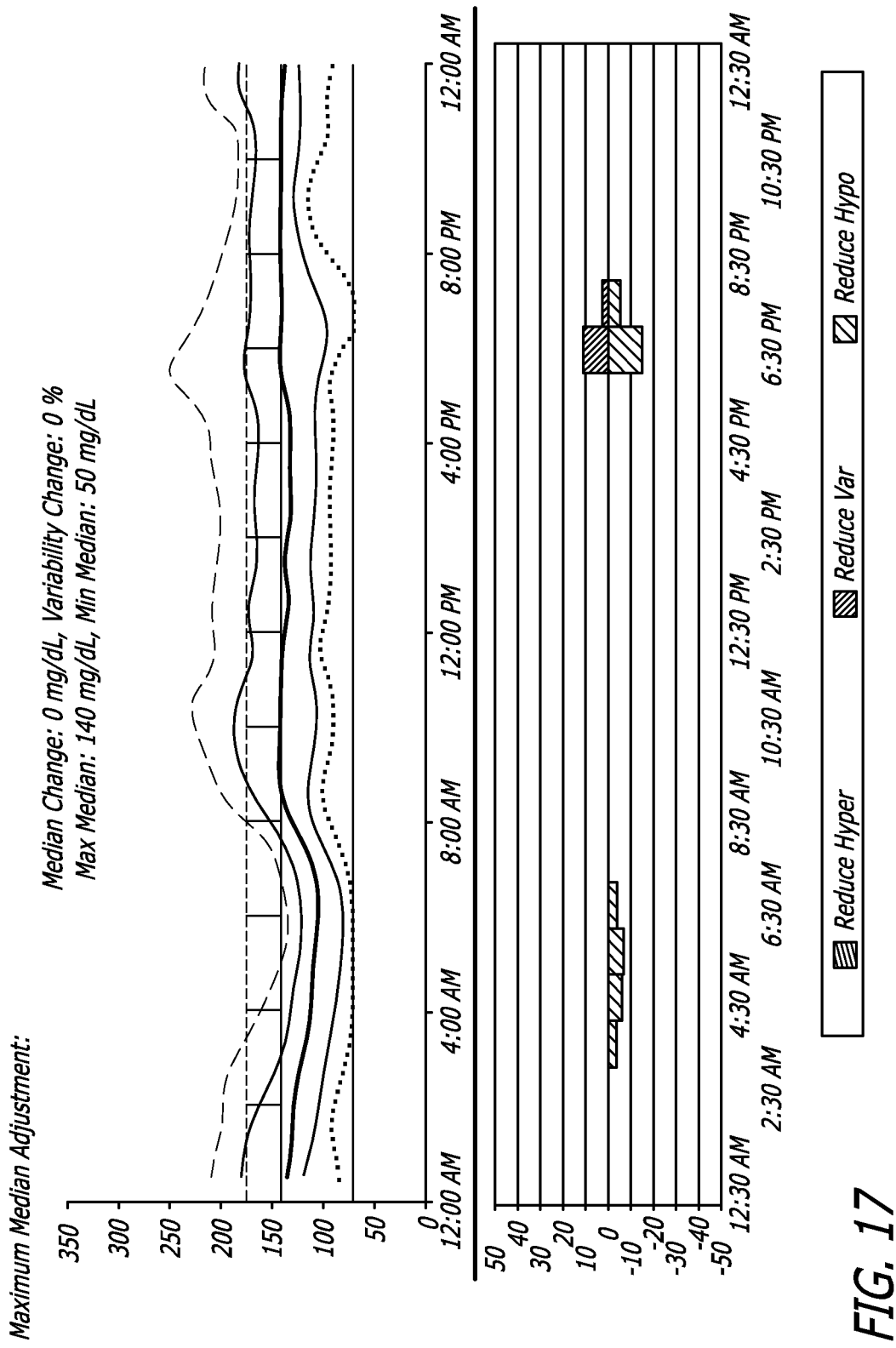
FIG. 17 presents a pair of displays of Maximum Median Adjustment having added visual features.
Figure 18:
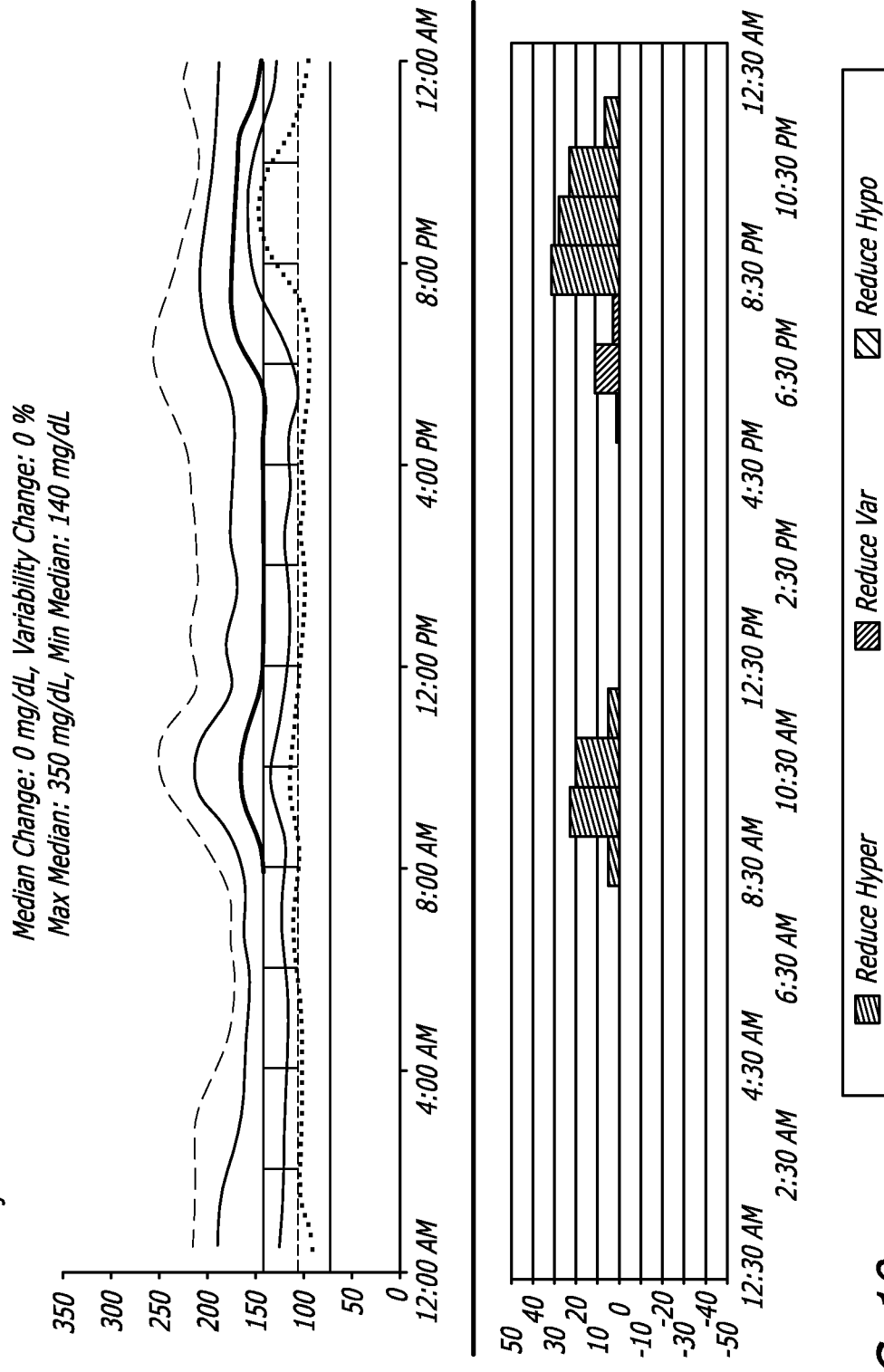
FIG. 18 presents a pair of displays of Minimum Median Adjustment having added visual features.

As an example, four controls are proposed: Median Adjustment, Variability Adjustment, Maximum Median Adjustment, and Minimum Median Adjustment. These may take the form of "scrollbars" for example. In addition, as the controls are adjusted, additional visual features may be added to the graph to emphasize what is being changed and by how much. For example, solid horizontal lines for "new" settings, dashed horizontal lines for "previous" settings, and vertical red lines to fill the space between the "previous" and "new." Below are examples of each control with added visual features:

FIG. 15 presents a display of Median Adjustment having added visual features, with the Median change at −26 mg/dL, Variability change of 0%, the maximum Median of 350 mg/dL, and the minimum Medial of 50 mg/dL;

FIG. 16 presents a display of Variability Adjustment having added visual features, with the Median change at 0 mg/dL, Variability change of −46%, the maximum Median of 350 mg/dL, and the minimum Medial of 50 mg/dL;

FIG. 17 presents a display of Maximum Median Adjustment having added visual features, with the Median change at 0 mg/dL, Variability change of 0%, the maximum Median of 140 mg/dL, and the minimum Medial of 50 mg/dL;

FIG. 18 presents a display of Minimum Median Adjustment having added visual features, with the Median change at 0 mg/dL, Variability change of 0%, the maximum Median of 350 mg/dL, and the minimum Medial of 140 mg/dL;

Touch Screen Controls

With the widespread adoption of touchscreen devices, these controls may be embedded into the graph itself. For example, placing and dragging a single finger in the plot area could activate the Median Adjustment control, with the vertical component of dragging motions being applied as the Median Adjustment. Placing two fingers in a "pinching" position on the plot area could activate the Variability Adjustment control, with "closing" and "opening" decreasing and increasing the variability, respectively. The Maximum Adjustment control could be activated by placing a finger above and outside of the plot area and dragging down into the plot area. Similarly, the Minimum Adjustment control could be activated by placing a finger below and outside of the plot area and dragging up into the plot area.

Figure 19:
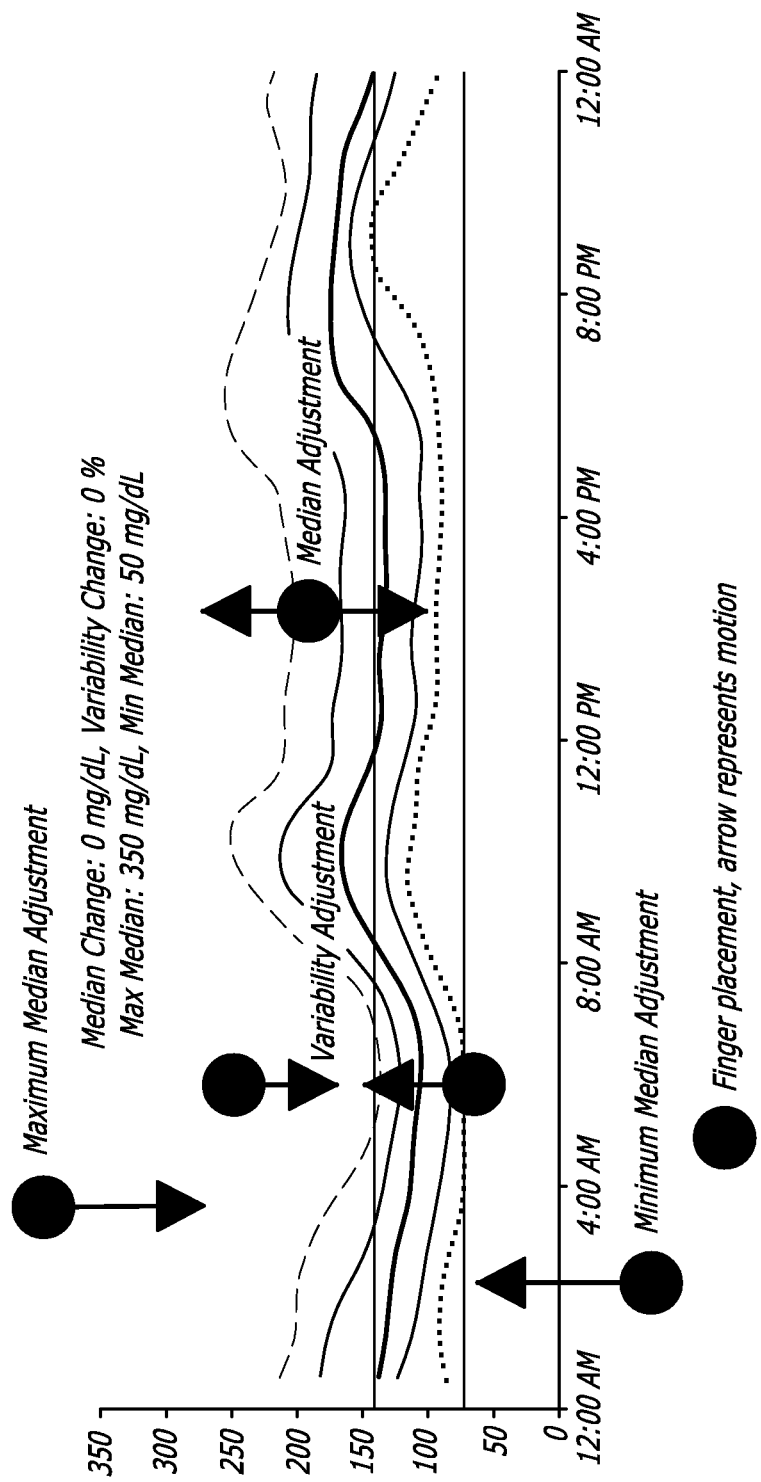
FIG. 19 shows a touchscreen display with examples of finger touchscreen controls.

Such touchscreen controls are shown on FIG. 19 by grey circles with arrows. In particular, finger placement shown with the grey circles includes Maximum Median Adjustment, Minimum Median Adjustment, Variability Adjustment, and Median adjustment. Other controls are possible.

Continuing with a system and method related to hypoglycemia and hyperglycemia determination, there is also provided an improved estimate of average glucose using HbA1c and CGM. In this aspect, CGM data is used to more accurately describe the relationship between average glucose and HbA1c results. The relationship between HbA1c and average glucose is variable from person to person. In spite of this, clinicians use one "population average" equation to relate one to the other. However, CGM data yields a good independent estimate of average glucose which, in tandem with HbA1c results, allows the development of an equation tailored to an individual.

HbA1c is a test that indicates average blood sugar over the past eight to twelve weeks. Its value, in percentage, is linked to average blood sugar, in mg/dL, by the following equation:

$$\text{Average Glucose (mg/dL)} = 28.7 \cdot \text{HbA1c (\%)} - 46.7 \qquad (1)$$

This is an average relationship based on a population of people; the relationship for individual subjects varies significantly. It has been determined, however, that individual relationship deviation from the average relationship is constant over time, and can be calculated provided that an independent estimate of the average glucose can be obtained.

When individual glucose data is provided by finger sticks, there are often not enough values to provide a good estimate of the average glucose. Thus, the results of an A1c test are converted to average glucose via Equation (1), and can be used to check the average finger stick glucose. Any significant discrepancies are blamed on meter inaccuracy or insufficient data.

If instead a CGM system is used to collect data, the average glucose value can be calculated with more confidence. A significant difference between this value and the value provided by the A1c test can be ascribed to individual variation from Equation (1), and corrected coefficients to Equation (1) can be estimated. This correction can take the form of an altered slope and/or an offset. If a slope and an offset must be found, then a minimum of two A1c tests taken several months apart, along with CGM for the same time periods, must be used. If two tests are taken, we have $$G_1 = m*A_1 + b, \text{ and } G_2 = m*A_2 + b \quad (2)$$

and slope, m, and offset, b, can be determined from the CGM average glucose, G, and the measured A1c, A. If there are more than two A1c tests and contemporaneous CGM traces, fitting a 1st order polynomial, by least squares for example, will determine the slope and offset. The independent variable in the least squares calculation is the more accurate measurement of the two.

Given a slope and an offset, Equation 2 can be used to estimate the average glucose for an individual patient based on A1c measure for that same period. If finger sticks are also available, blood glucose values can be combined by using a weighted average. It is necessary to estimate how many finger sticks an A1c measurement is equivalent to. Once this is done, the weights for the average are obvious. In addition, the median glucose is now easily calculated.

Any estimate has inherent uncertainty. If CGM use coincides with multiple A1c tests, the uncertainty in the modified coefficients can be quantified. In any case, the use of Equation (2) will make subsequent estimates of average glucose from measured A1c more accurate. In addition, the Equation (2) can be used "in reverse" to provide more accurate estimates of A1c from finger stick values when a current A1c test result is not available. Also, note that if three or more A1c tests are available, along with CGM during the same time period, then least squares techniques may be used to determine the best values for m and b. Also, note that models other than the two parameter linear model may be used to define the relationship between average glucose and A1c.

If the subject reverts to using finger sticks, Equation (2) can be used to make a more accurate estimate of the average glucose. This can be used as the average glucose value in any subsequent analysis. This allows us to specialize finger stick use to estimate only variability. Finger stick timing could be adjusted, relative to meals for example, to produce an estimate of variability that agrees with the estimate from the CGM. However, this might make the finger stick estimate of the average glucose very inaccurate.

If the finger stick estimate of the average glucose is still accurate enough, disagreement between the average glucose from A1c and the glucose average derived from finger sticks can be used as a data quality or data insufficiency test. The significance of the deviation can be determined from the uncertainty in the estimates of the coefficients of Equation (2).

In yet another aspect of the invention, a theoretical calculation of glycemic risk based on the observation that CGM data follows a probability distribution is provided.

Variability is known to be a risk factor for hypo-hyperglycemia. However, since variability is difficult to characterize and measure, it has largely been ignored, especially in determining treatment dosages. The invention uses the observation that glucose levels follow a probability distribution over time to quantify glycemic risk. Thus, variability is shown to be as important as average glucose level.

A glycemic target range is a common way to measure and encourage glucose control. All glucose values below the lower limit are considered to be hypoglycemic, and all values above the upper limit are considered to be hyperglycemic. There are many ways of using glucose values to assess the risk of hypo- and hyperglycemia. The invention describes a way of using an assumed distribution of glucose values to theoretically calculate measures of hypoglycemic and hyperglycemic risk, and considers certain extensions such as time correlation and bias correction.

Glycemic risk calculations can be divided into two broad classes: parametric and nonparametric. A parametric calculation assumes that the glucose values follow a distribution, a Lognormal or a Gamma distribution for example, and uses the data to calculate the parameters of the distribution. We have found that the most practical distributions are determined by two parameters (mean and standard deviation, usually), however, there are distributions that need fewer or more parameters to define them, and they could also be used. From these parameters, all glycemic risk estimates can be derived. A nonparametric calculation does not assume any distribution. The risk estimate is calculated directly from the data. The advantage of a parametric calculation is that less data is required to make a reasonable estimate. The disadvantage is that the data must follow the assumed distribution.

Although less data is necessary to make a parametric estimate, a relatively large data set is necessary to establish the validity of such a model. For example, if we think that that glucose values fit a normal distribution, it takes a lot of data from many subjects to confirm the hypothesis. CGM makes it practical to collect data in the necessary quantities.

Most glycemic risk estimates involve the rate of accumulation of data points beyond a single threshold, either hypoglycemic or hyperglycemic; for example, we could use the area of data below the hypo threshold per week.

The general nonparametric formula for risk is:

$$R = \frac{\text{Sampling Interval}}{\text{Collection Time}} \sum_i |G_i - G_0|^n$$

where only the data points ($G_i$) beyond the threshold ($G_0$) are included in the sum, but the collection time includes all data points. The exponent, n, can take nonnegative values. Larger values of n weight more extreme data points more heavily. For example, if n=0, all points beyond the threshold are weighted equally and R is the fraction of points beyond the threshold. If n=1, R is the rate of area accumulation beyond the threshold; points are weighted according to their distance from the threshold.

The parametric formula for hypo risk is:

$$R_L = \int_0^{G_L} (G_L - x)^n P(x) dx$$

The hyper risk formula is similar:

$$R_H = \int_{G_H}^{\infty} (x - G_H)^n P(x) dx$$

Here, P(x) is the assumed distribution with the distribution parameters determined by the data; $G_L$ and $G_H$ are hypo- and hyperglycemic thresholds. Here, as with the nonparametric formula, a larger values of n weights the more extreme values more heavily. Note that if there are no data values beyond a threshold, the nonparametric formula yields R=0, while the parametric formula always gives a positive result.

One pair of nonparametric glycemic metrics that does not follow the previous discussion is LBGI and HBGI, as defined by Boris Kovatchev and William Clarke, et al., *Quantifying Glucose Variability in Diabetes via Continuous Glucose Monitoring: Mathematical Methods and Clinical Application*, Diabetes Technology and Therapeutics, 2005; 7:849-862. Here, the hypo and hyper limits coincide at 112.5 mg/dL and a complicated weighting of the distance from the threshold is used in the sum. For this case, we can apply the same parametric formulas:

$$R_L = \int_0^{G_L} f(x) P(x) dx$$

where f(x) is the LBGI function for a single glucose value. The formula for $R_H$ is analogous.

So far, all of the formulas in this paper have ignored possible time correlations. One elaboration of the nonparametric method is to insist that a minimum amount of time be spent beyond a threshold before the subject is considered to be out of euglycemia. This will also provide some protection from measurement artifacts.

For example: suppose the hypo threshold is 70 mg/dL. The subject is not considered to have entered hypoglycemia unless he has spent:

60 continuous minutes at or below 70 mg/dL, or
40 continuous minutes at or below 60 mg/dL, or
30 continuous minutes at or below 50 mg/dL, or
20 continuous minutes at or below 40 mg/dL.

Here, we have assumed a sampling interval of ten minutes. No single data point, no matter how extreme, can contribute to the hypoglycemic risk. Once in hypo, subsequent points below the threshold add to the risk. There is a similar constraint to leaving hypoglycemia: no isolated data point above the hypo threshold can take the subject out of hypo.

The parametric formulas do not include time. Data is used only to calculate the distribution parameter values. Thus, time correlations cannot be included in the parametric method.

One important difference between parametric and nonparametric methods has been mentioned: parametric methods use data more efficiently. We will now expand on this idea. Glucose data is used to make estimates of glycemic risk. Inherent in the idea of estimate is uncertainty: how close to the "truth" do we expect our estimate to be? If we had densely sampled data, we could calculate the true value of any of our defined risks using the nonparametric formulas.

If a relatively sparse subsample of this data is available, an estimate of the risk can be made. As the number of data points decreases, the estimate uncertainty increases. The magnitude of the uncertainty seems to scale as the reciprocal of the square root of the number of data points. These nonparametric estimates are unbiased. If a number of different samples are taken from the complete set of data, the average of the estimates converges to the truth as the number of estimates increases, or as the sample size increases.

Parametric estimates are different. The uncertainty in the estimate for a given sample size is less than for nonparametric estimates, but the parametric estimator might not be unbiased. This remains true even when all of the data is used. The value of the bias can be found by assuming that the true value is found using the nonparametric method with many data points. This "truth" is compared to results obtained from the parametric method using a certain number of points collected during a certain portion of the day. We find that the bias is a function of sample size and time of day. Compensating for this bias will increase the accuracy of a parametric estimate.

Data collection compliance is always an issue. The ability to get a useful result with relatively few samples is an important advantage. In addition to using a parametric method, we can also use a Structured Test Protocol (STP) to get the most from each data point. With STP, we define preferred times of testing, the number of tests per day, and the number of days. The test times can be defined either relative to a meal or by the clock. We have tried eight tests per day over seven days, ranging from before breakfast to four hours after dinner, with good results. We have also tried four tests per day over seven days. With half the number of points, the uncertainty is larger, but the results are still clinically useful.

Thus, parametric models are more efficient in their use of data than nonparametric methods, making it possible to obtain useful predictions with Structured Test Protocols of finger sticks in a reasonable number of days. CGM data enables the construction of parametric models by providing the large numbers of data points.

A further aspect of the invention involves tailoring SMBG test schedules based on results from CGM wear. The invention uses the results of brief periods of CGM wear to generate SMBG test schedules that focus on periods of high variability and hypoglycemia risk discovered by analysis of the CGM data. The invention maximizes the utility of SMBG testing by focusing SMBG test schedules on periods of high variability and hypoglycemic risk.

Some of the problems with SMBG testing schedules are patient compliance and limited data. Patients may not comply with an SMBG testing schedule because BG testing can be painful and inconvenient. In order to maximize compliance, SMBG test schedules generally occur over a short time period with just a handful of SMBG tests. This leads to the second problem, limited data. Blood glucose testing schedules will produce relatively small data sets which can introduce a high uncertainty to the calculated median glucose, calculated low range variability, and calculated hypoglycemia risk. The higher the uncertainty, the less aggressive treatment recommendations can be in order to be sure that the hypoglycemia risks are avoided.

Additionally, another problem caused by collecting a small amount of data is that SMBG measurements can either be focused on a small amount of small time periods or large time periods, but not both. For example, an SMBG test schedule might focus on median and variability at fixed times, for example one hour after meals, requiring the patient to perform tests every day for one to two weeks, one hour after each scheduled meal. With such a test schedule, the median and low range variability can be calculated relatively accurately, but only for one hour after each scheduled meal. Little information will be learned about other time periods (such as two hours after each meal). Alternatively, the SMBG test schedule may follow a progressive schedule requiring the patient to test at various times of the day. For example the schedule might ask for the patient to test at 7:00 AM, 11:00 AM, 3:00 PM, and 7:00 PM one day, 8:00 AM, 12:00 PM, 4:00 PM, 8:00 PM the next, etc., for the one to two weeks. This type of SMBG test schedule can produce a relatively accurate portrayal of Median and Low Range Variability during the entire range of times tested (note: it is unlikely that a patient will comply with a testing schedule that requires a test during sleeping hours day after day), however calculations of Median glucose, Low Range Variability and Hypo Risk will have a very high uncertainty for any specific time of day.

The invention tailors the test schedules to focus on problem times (times of high variability or hypoglycemic risk) discovered by a short period of continuous glucose monitor wear. This addresses the issues of limited data and compliance because the SMBG schedules can be shorter, thus leading to greater compliance, and the data that is collected is the important data, which derives more value from the limited supply of data. Additionally, by identifying the time periods of interest it can help identify when it is appropriate to focus on small time periods, and which ones, and when it is appropriate to focus on larger time periods.

SMBG testing schedules are assigned to patients by HCPs in order to gather data so that the HCPs can make recommendations to patients regarding therapy and lifestyle changes. Key metrics that can be ascertained by this SMBG testing are median glucose, Low Range Variability and Hypoglycemia Risk. Typically a key therapy goal is reduce a patient's median glucose while avoiding the risk of the patient spending significant time in hypoglycemia or experiencing a severe hypoglycemia incidence. The higher a patient's Low Range Variability, the higher the Median glucose the patient will need to maintain in order to avoid these incidences of hypoglycemia.

Continuous Glucose Monitors are also given to patients by HCPs in order to measure a patient's Median glucose, Low Range Variability, and Hypoglycemia Risk. Using a Continuous Glucose Monitor most of the problems associated with Discrete Blood Glucose ("DBG") testing can be addressed. With a continuous blood glucose monitor, a problem with patient compliance typically does not exist. There is enough data to measure Low Range Variability to very small time periods, typically as short as one hour. Additionally, CGM systems provide data while the patient is sleeping. The drawbacks of Continuous glucose monitoring are that it is expensive, it can be uncomfortable, and that patients must typically wear a device all the time, which many are very reluctant to do.

This invention supposes that HCPs will only prescribe continuous monitors for short time periods. It proposes that the results from the CGM wear be used to tailor specific SMBG test schedules that target the areas of interest (usually times of high Low Range Variability, or hypoglycemia) identified by analysis of the CGM data. The tailored SMBG test schedule may be used to monitor the effect of lifestyle or therapy changes prescribed by the HCP, or it may simply be used to monitor more closely an ongoing problem, Note: in the cases mentioned below, the use of progressive and fixed time SMBG testing schedules are mentioned. Many of the cases mentioned below confine all testing to specific time periods. In these cases it may not be too onerous to increase the number of tests per time period as the overall number of tests will not increase.

Possible Issues Identified by CGM Results and SMBG Tailored Test Schedules

1. CGM Identified Issue—The CGM identifies that Low Range Variability and Hypo Risk are scattered throughout the day with nothing distinguishing any particular days or time periods.
   Tailoring—Assign a progressive SMBG schedule as previously described: ask for the patient to test at 7:00 AM, 11:00 AM, 3:00 PM, and 7:00 PM one day, 8:00 AM, 12:00 PM, 4:00 PM, 8:00 PM the next . . . etc. for the 1 to two weeks.
2. CGM Identified Issue—The CGM identifies that there is high Low Range Variability between specific meal times or during the fasting period, with no recurring patterns regarding days of the week and the period of time of the variability cannot be more specifically specified.
   Tailoring—Assign a progressive SMBG schedule as previously described, but confine it to the in between meal periods (or fasting) of interest. If some time periods do not display variability then no testing need be done in those time periods which means either a shorter SMBG schedule for the patient or alternatively more tests can be scheduled within the periods of interest, thus producing more accurate results.
3. CGM Identified Issue—The CGM identifies that low range variability occurs during short time periods between meals. Example, one hour after certain meals.
   Tailoring—Assign a fixed time SMBG schedule around the time periods of interest. For example in the case where variability occurs about 1 hour after lunch, assign an SMBG test schedule which asks for tests distributed over that specific time period.
4. CGM Identified Issue—The CGM identifies areas of high low range variability and/or hypo risk during specific hours of the day (ex. 4 AM-5 PM).
   Tailoring—Schedule tests that during a one to two week period occur at various times during the 4-5 PM window (ex. 3:45 PM-5:15 PM). The results of this testing should produce relatively accurate information regarding the patient's hypoglycemia incidences and low range variability during this time. Note, this concept can be extended to sleeping hours if severe frequent incidences of severe hypoglycemia are detected. One would assume that a patient who frequently experiences severe hypoglycemia incidences will be motivated to test even during sleep hours due to the risk of coma and death during these instances. For example, if the time interval of interest is 4:00 AM to 5:00 AM a similar SMBG test schedule can be created. Having this tailored test schedule limits the inconvenience of having to wake up during sleep.
5. CGM Identified Issue—The CGM identifies areas of high Low Range Variability during specific days of the week (for example, Saturdays).
   Tailoring—Assign SMBG testing to the day of interest. For example, the patient should be asked to test one day a week (for example, Saturday) for five to ten weeks with tests scattered at various times through the day.
6. CGM Identified Issue—The CGM identifies areas of high Low Range Variability or hypoglycemia incidences during specific days of the week at specific times (for example, 6 PM-8 PM on Saturdays).
   Tailoring—Assign SMBG testing to those specific hours of the specific days of interest.
7. CGM Identified Issue—The CGM identifies post prandial peak time of meals. Example embodiment: Divide data into different meal segments, or to rely on patient's meal marker input, or a combination of both. Analyze each meal segment data to obtain a distribution of time-to-peak durations. For segments that lack a meal marker, the start is identified as the average timestamp of the $5^{th}$ percentile glucose value in that segment, and the peak is identified as the average timestamp of the $95^{th}$ percentile glucose value in that segment.
   Tailoring—Set SMBG test reminder at the optimal duration after a meal-related SMBG event marker. Different meal times may require different duration settings.
8. CGM Identified Issue—Analysis of CGM finds patterns in the data taken when it would be convenient to test (e.g. during waking hours) such as values at specific times [absolute or meal-relative] or fluctuations in value [rises/falls of a specific magnitude or rate] at specific times which correlate to observed problems at future times when it would be less convenient to test (e.g. overnight).

Tailoring—Prompt for readings at appropriate times to establish presence of predictive pattern, and if readings detect the pattern act more aggressively to detect or prevent the future problem (e.g. suggest immediate preventative action or schedule prompts during anticipated problem period).

In another embodiment of this invention the results of CGM testing may be used to tailor a maintenance SMBG test schedule. A maintenance SMBG test schedule is used at times when data is not being is not being collected to help diagnose the state of a patient's diabetes, rather it is used to ensure that the patient is maintaining good control when other more comprehensive monitoring is not taking place. The results of CGM testing may identify a few specific times of day of high low range variability or excessive hypoglycemia risk. In this case the maintenance schedule can be tailored for testing at those specific times of day.

Figure 20:
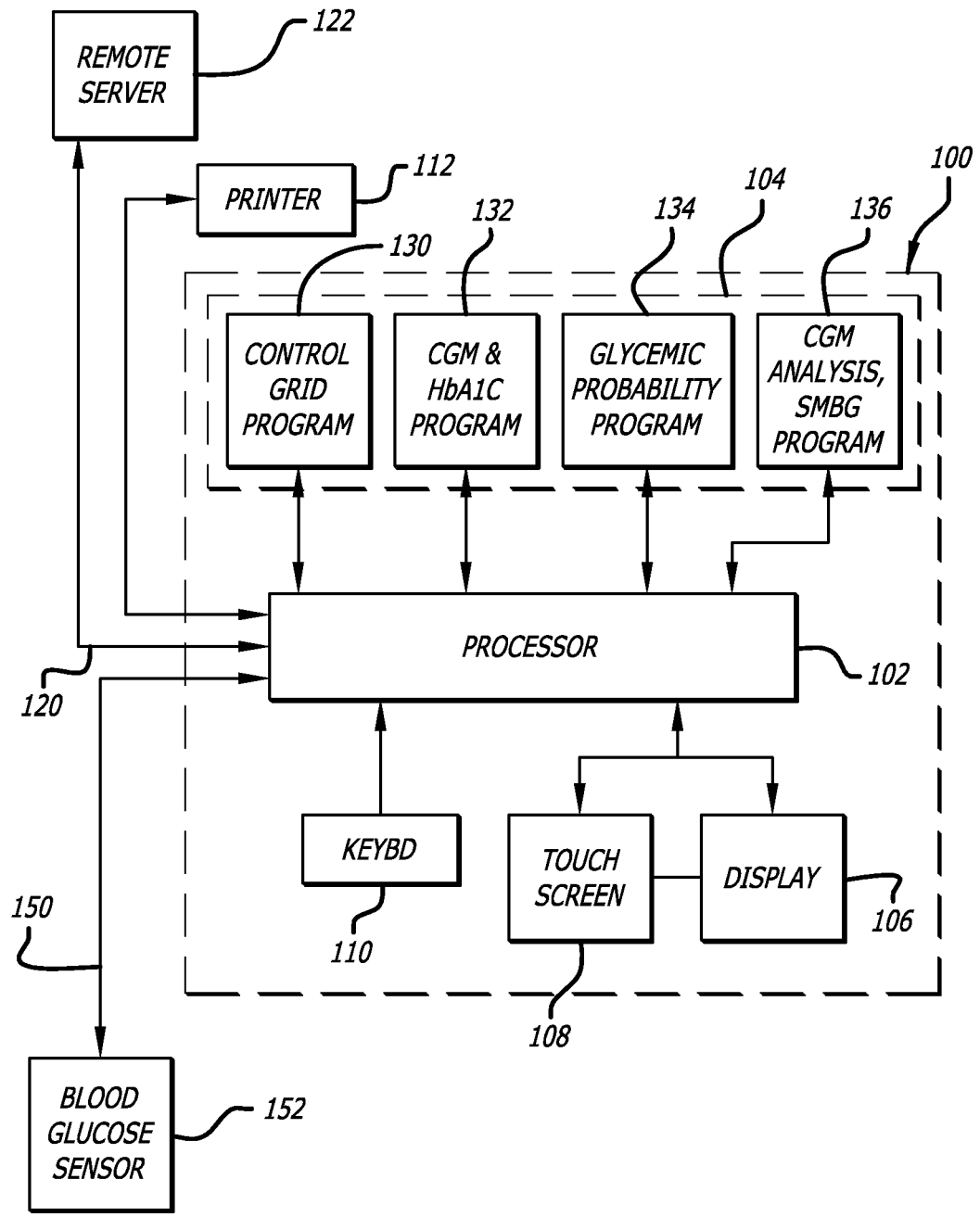
FIG. 20 is a block diagram of an embodiment of a system and method for carrying out the invention.

FIG. 20 is a block diagram of an embodiment of a system and method 100 for carrying out the invention. This embodiment includes a processor 102 housed in a mobile or stationary device at the patient site, a non-volatile memory 104 for storing a program or programs used to program the processor, a visual display 106 for visual output, the display having in this embodiment a touch-screen 108 for input, and a keyboard input device 110 of other type of device usable to manual entry, such as a keypad. The system 100 is connected to a printer 112 as an output or display device, and has a data output 120 for communicating to a remote server 122. In one embodiment, the remote server stores in a memory a patient's data for remote access by an HCP. In an embodiment, the processing of data is performed in the patient processor, or may be performed at the remote server.

The memory 104 includes, in this embodiment, the Control Grid Program 130 for calculation and visualization of glycemic risks, the CGM and HbA1c program 132 for producing improved estimates of average glucose, the Glycemic Probability program 134 for estimating glycemic risk, and the CGM Analysis and SMBG schedule tailoring program 136, all of which are described above in detail. Other programs and data bases may be stored in the non-volatile memory. In another embodiment, one or more of the programs may be stored elsewhere but may be executed in the processor 102. Other arrangements are possible and other hardware variations to carry out the invention are possible.

Blood glucose data 150 is provided by a blood glucose sensor 152. The BG sensor 152 may take the form of a continuous glucose monitor (CGM) or may take other forms such as a strip reader, or other.

In the present description, the terms component, module, device, may refer to any type of logical or functional process or blocks that may be implemented in a variety of ways. For example, the functions of various blocks can be combined with one another into any other number of modules. Modules can be implemented as a software program stored on a tangible memory (e.g., random access memory, read only memory, CD-ROM memory, hard disk drive, or others) to be read by a processor, or central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. The modules can be implemented using special purpose instructions (SIMD instructions or others), field programmable logic arrays, or any mix thereof or others which provides the desired level performance and cost.

As disclosed herein, implementations and features of the invention may be implemented through computer-hardware, software and/or firmware. For example, the systems and methods disclosed herein may be embodied in various forms including, for example, a data processor, such as a computer that also includes a data base, digital electronic circuitry, firmware, software, or in combinations of them. Further, while some of the disclosed implementations describe components such as software, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various processes and operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Further implementations and/or variations may be provided in addition to those set forth herein. For example, the present invention may be directed to various combinations and sub-combinations of the features disclosed in the detailed description of preferred embodiments.

While the system and method have been described in terms of what are presently considered to be specific embodiments, they need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A system for displaying glycemic information and risk, the system comprising:
   a non-volatile memory in which is stored a glucose data processing program configured to program a processor to analyze received glucose data of a person and from the analysis, produce a display;
   a display device; and a processor, coupled with the nonvolatile memory and the display device, the processor being configured to access the memory to load and run in the processor the glucose data processing program to analyze glucose data, wherein the processor is programmed to:
  analyze the received glucose data to determine a plurality of glucose medians, low range variability of glucose, and hypoglycemia risk; and
  cause the display device to visually present a first display and a second display at the same time,
  wherein the first display comprises a graph having a vertical axis representing glucose levels, a horizontal axis representing a plurality of times of the day, and a plot of the glucose median of received glucose data across the plurality of times of the day, and
  wherein the second display comprises a plurality of hypoglycemia risk indicators and a plurality of variability risk indicators,
  wherein each hypoglycemia risk indicator indicates an amount of risk that hypoglycemia will occur in a different segment of time within the plurality of times of the day and each hypoglycemia risk indicator has a horizontal position within the second display that corresponds to the position of that different segment of time within the plurality of times of the day, and
  wherein each variability risk indicator indicates an amount of low range glucose variability in a different segment of time within the plurality of times of the day and each variability risk indicator has a horizontal position within the second display that corresponds to the position of that different segment of time within the plurality of times of the day.

2. The system of claim 1, wherein the glucose data processing program further programs the processor to control the display device to visually present, at a different time from the first and second displays, a control grid on which is shown a hypoglycemia risk curve, a glucose variability curve, and risk reduction distances for hypoglycemia and glucose variability.

3. The system of claim 2, wherein the glucose data processing program further programs the processor to control the display device to visually present on the control grid a treatment recommendation point.

4. The system of claim 2, wherein the glucose data processing program further programs the processor to control the display device to visually present on the control grid an uncertainty boundary.

5. The system of claim 2, wherein the glucose data processing program further programs the processor to control the display device to visually present on the control grid a hyperglycemia curve and a risk reduction distance for hyperglycemia.

6. The system of claim 1, wherein the system further comprises a touch screen associated with the display device,
  wherein the glucose data processing program further programs the processor to visually present changes in one or more of the plurality of hypoglycemia risk indicators resulting from input from the touch screen representing alteration in the glucose median and/or a glucose variability.

7. The system of claim 1, wherein the glucose data processing program further programs the processor to:
  analyze received HbA1c data with the glucose data;
  determine an estimate of average glucose; and
  control the display device to visually present the estimate of average glucose.

8. The system of claim 1, wherein the glucose data processing program further programs the processor to subject the glucose data to an analysis of probability distribution in determining glycemic risk.

9. The system of claim 1, wherein the glucose data processing program further programs the processor to control the display device to visually present how a self-monitoring blood glucose (SHBG) test schedule may be tailored to obtain further desired glucose data.

10. The system of claim 1, wherein the glucose data processing program further programs the processor to cause the display device to visually present the first display on an upper portion of a display screen and the second display on a lower portion of the display screen.

11. The system of claim 1, wherein each hypoglycemia risk indicator has a shape with a size that indicates the amount of risk that hypoglycemia will occur and wherein each variability risk indicator has a shape with a size that indicates the amount of risk of low range glucose variability.

12. The system of claim 1, wherein a first one of the plurality of hypoglycemia risk indicators indicates the amount of risk that hypoglycemia will occur in a first segment of time within the plurality of times of the day and is vertically-aligned with a first one of the plurality of variability risk indicators that indicates the amount of low range glucose variability in the same first segment of time.

13. A method for displaying glycemic information and risk, the method comprising:
  receiving glucose data;
  analyzing, with a processor, the received glucose data to determine a glucose median, low range variability of glucose, and hypoglycemia risk;
  displaying a first display comprising a graph having a vertical axis representing glucose levels, a horizontal axis representing a plurality of times of the day, and a plot of the glucose median of received glucose data across the plurality of times of the day; and
  displaying a second display at the same time as the first display, wherein the second display comprises a plurality of hypoglycemia risk indicators and a plurality of variability risk indicators,
  wherein each hypoglycemia risk indicator indicates an amount of risk that hypoglycemia will occur in a different segment of time within the plurality of times of the day and each hypoglycemia risk indicator has a horizontal position within the second display that corresponds to the position of that different segment of time within the plurality of times of the day, and
  wherein each variability risk indicator indicates an amount of low range glucose variability in a different segment of time within the plurality of times of the day and each variability risk indicator has a horizontal position within the second display that corresponds to the position of that different segment of time within the plurality of times of the day.

14. The method of claim 13, further comprising:
  displaying, at a different time from the first and second displays, a third display comprising a control grid with a hypoglycemia risk curve, a glucose variability curve, and risk reduction distances for hypoglycemia and glucose variability.

15. The method of claim 14, further comprising:
  displaying on the control grid a treatment recommendation point.

16. The method of claim 14, further comprising:
  displaying on the control grid an uncertainty boundary.

17. The method of claim 14, further comprising:
  displaying on the control grid a hyperglycemia curve and a risk reduction distance for hyperglycemia.

18. The method of claim 13, further comprising:
receiving input from a touch screen and displaying changes in hypoglycemia risk resulting from the input from the touch screen representing alteration in the glucose median and/or a glucose variability.

19. The method of claim 13, further comprising:
receiving HbA1c data;
analyzing, with the processor, the HbA1c data with the glucose data;
determining, with the processor, an estimate of average glucose; and
displaying the estimate of average glucose.

20. The method of claim 13, further comprising:
performing an analysis of probability distribution on the glucose data to determine glycemic risk.

21. The method of claim 13, further comprising:
displaying how a self-monitoring blood glucose (SHBG) test schedule may be tailored to obtain further desired glucose data.

22. The method of claim 13, further comprising displaying the first display on an upper portion of a display screen and displaying the second display on a lower portion of the display screen.

23. The method of claim 13, wherein each hypoglycemia risk indicator has a shape with a size that indicates the amount of risk that hypoglycemia will occur and wherein each variability risk indicator has a shape with a size that indicates the amount of risk of low range glucose variability.

24. The method of claim 13, wherein a first one of the plurality of hypoglycemia risk indicators indicates the amount of risk that hypoglycemia will occur in a first segment of time within the plurality of times of the day and is vertically-aligned with a first one of the plurality of variability risk indicators that indicates the amount of low range glucose variability in the same first segment of time.

* * * * *